US008106214B2

(12) United States Patent
Rueckle et al.

(10) Patent No.: US 8,106,214 B2
(45) Date of Patent: Jan. 31, 2012

(54) 2-IMINO-4-(THIO)OXO-5-POLYCYCLOVINYLAZOLINES FOR USE AS PI3 KINASE INHIBITORS

(75) Inventors: Thomas Rueckle, Plan-les-Ouates (CH); Jeffrey Shaw, Vessy (CH); Dennis Church, Commugny (CH); David Covini, Neydens (FR)

(73) Assignee: Merck Serono SA, Coinsins (CH)

( * ) Notice: Subject to any disclaimer, the term of this patent is extended or adjusted under 35 U.S.C. 154(b) by 336 days.

(21) Appl. No.: 10/565,976

(22) PCT Filed: Jul. 27, 2004

(86) PCT No.: PCT/EP2004/051625
§ 371 (c)(1),
(2), (4) Date: Apr. 28, 2006

(87) PCT Pub. No.: WO2005/011686
PCT Pub. Date: Feb. 10, 2005

(65) Prior Publication Data
US 2007/0021447 A1 Jan. 25, 2007

(30) Foreign Application Priority Data
Jul. 28, 2003 (EP) .................................. 03102313

(51) Int. Cl.
*C07D 277/04* (2006.01)
*A61K 31/425* (2006.01)
(52) U.S. Cl. ........................................ 548/184; 514/369
(58) Field of Classification Search .................. 548/184; 514/369
See application file for complete search history.

(56) References Cited

U.S. PATENT DOCUMENTS

| 5,750,712 | A * | 5/1998 | Yoneda et al. ................. 548/186 |
| 7,842,698 | B2 | 11/2010 | Rueckle et al. |
| 2006/0293338 | A1 * | 12/2006 | Hasegawa et al. ......... 514/254.02 |
| 2009/0306069 | A1 | 12/2009 | Rueckle et al. |

FOREIGN PATENT DOCUMENTS

| EP | 0 697 410 | 2/1996 |
| JP | 5-2200 | 1/1993 |

OTHER PUBLICATIONS

Hasegawa et al. (PGPUB 2006/0293338 CAPLUS Abstract Accession # 2004:467698).*
Vasa et al. (CAPLUS Abstract of: Journal of the Indian Chemical Society (1959), 36, 648-50).*
Unangst et al. (J. Med. Chem., 1994, vol. 37, No. 2, p. 322-28).*
Roue, Nathalie et al., "Synthesis of the marine alkaloid leucettamine B", Tetrahedron, vol. 55, No. 51, pp. 14729-14738, 1999.
Brummond, Kay M. et al., "Solid-Phase Synthesis of BRL 49653", J. Org. Chem., vol. 64, pp. 1723-1726, 1999.
Fraser, et al., "Regulation of Interleukin-2 Gene Enhancer Activity by the T Cell Accessory Molecule CD28", Science, vol. 251, pp. 313-316, 1991.
Fruman, David A. et al., "Phosphoinositide Kinases", Ann. Rev. Biochem, vol. 67, pp. 481-507, 1998.
Gerard, Craig et al., "Chemokines and disease", Nature Immunology, vol. 2, No. 2, pp. 108-115, 2001.
Hirsch, Emilio et al., "Resistance to thromboembolism in PI3Kγ-deficient mice[1]" FASEB, vol. 15, Part 11, pp. 2019-2021, 2001.
Hirsch, Emilio et al., "Central role for G protein-coupled phoshoinositide 3-Kinase y in inflammation", Science, vol. 287, Part 5455, pp. 1049-1053, 2000.
Lopez-Ilasaca, Marco et al., "Phosphoinositide 3-Kinase y is a mediator of Gβγ-dependent jun kinase activation", The Journal of Biological Chemistry, vol. 273, No. 5, pp. 2505-2508, 1998.
Janusz, John M. et al., "New cyclooxygenase-2/5-lipoxygenase inhibitors. 3. 7-tert-butyl-2, 3-dihydro-3, 3-dimethylbenzofuran derivatives as gastrointestinal safe antiinflammatory and analgesic agents: variations at the 5 position", Journal of Med. Chem., vol. 41, No. 18, pp. 3515-3529, 1998.
Katso, Roy et al., "Cellular function of phosphoinositide 3-Kinases: Implications for development, immunity, homeostasis, and Cancer,"Annu. Rev. Cell Dev. Biol., vol. 17, pp. 615-675, 2001.
Laffargue, Muriel et al., "Phosphoinositide 3-Kinase γ is an essential amplifier of mast cell function", Immunity, vol. 16, No. 3, pp. 441-451, 2002.
Lawlor, Margaret A. et al., "PKB/Akt: a key mediator of cell proliferation, survival and insulin responses", Journal of Cell Science, vol. 114, No. 16, pp. 2903-2910, 2001.
Leslie, Nick R. et al., "Phosphoinositide-regulated Kinases and Phosphoinositide phosphatases", Chem. Rev., vol. 101, No. 8, pp. 2365-2380, 2001.
Pages, Francoise et al., "Binding of phosphatidyl-inositol-3-OH kinase to CD28 is required for T-cell signalling", Nature, vol. 369, pp. 327-329, 1994.
Panayotou, George et al., "Phosphatidyl-inositol 3-kinase: a key enzyme in diverse signalling processes", Trends in Cell Biology, vol. 2, pp. 358-360, 1992.
Parker, Peter J. et al., "PI 3-kinase puts GTP on the rac", Current Biology, vol. 5, No. 6, 1995.
Rudd, Christopher E. et al., "Upstream-downstream: CD28 cosignaling pathways and T cell function", Immunity, vol. 4, pp. 527-534, 1996.
Stein, Robert C. et al., "PI3-kinase inhibition: a target for drug development?", Molecular Medicine Today, vol. 6, No. 9, pp. 347-357, 2000.
Stephens, Len, et al., "Roles of PI3Ks in leukocyte chemotaxis and phagocytosis", Current Opinion Cell. Biol., vol. 14, No. 2, pp. 203-213, 2002.
Thelen, Marcus et al., "Wortmannin binds specifically to 1-phosphatidylinositol 3-kinase while inhibiting guanine nucleotide-binding protein-coupled receptor signaling in neutrophil leukocytes", Proc. Natl. Acad. Sci, vol. 91, pp. 4960-4964, 1994.
Toker A. et al., "Phosphoinositides and signal transduction", Cellular and Molecular Life Sciences, vol. 59, No. 5, pp. 761-779, 2002.

(Continued)

*Primary Examiner* — Robert Havlin
(74) *Attorney, Agent, or Firm* — Oblon, Spivak, McClelland, Maier & Neustadt, L.L.P.

(57) ABSTRACT

The present invention is related to 2-imino-azolinone-vinyl fused-benzene derivatives of Formula (1) in particular for the treatment and/or prophylaxis of autoimmune disorders and/or inflammatory diseases, cardiovascular diseases, neurodegenerative diseases, kidney diseases, platelet aggregation, cancer, transplantation, graft rejection or lung injuries.

9 Claims, No Drawings

OTHER PUBLICATIONS

Vanhaesebroeck, B. et al., "Signaling by distinct classes of phosphoinositide 3-kinases", Experimental Cell Research, vol. 253, Part 1, pp. 239-254, 1999.

Vanhaesebroeck, Bart, et al., "Phosphoinositide 3-kinases: a conserved family of signal transducers", Trends Biochem. Sci., vol. 22, No. 7, pp. 267-272, 1997.

Wymann, Matthias P. et al., "Lipids on the move: phosphoinositide 3-kinases in leukocyte function", Immunology Today, vol. 21, No. 6, pp. 260-264.

Yao, Ryoji et al., "Requirement for phosphatidylinositol-3 kinase in the prevention of apoptosis by nerve growth factor", Science, vol. 267, pp. 2003-2006, 1995.

"Chemical Block Stock Library", XP002263803, 2003.

"ChemDiv Inc. Product Library", XP002263804, 2003.

U.S. Appl. No. 12/906,729, filed Oct. 18, 2010, Rueckle, et al.

* cited by examiner

2-IMINO-4-(THIO) OXO-5-POLYCYCLOVINYLAZOLINES FOR USE AS PI3 KINASE INHIBITORS

FIELD OF THE INVENTION

This present invention is related to the use of imino-azolinone-vinyl fused-benzene derivatives of Formula (I) for the treatment and/or prophylaxis of autoimmune disorders and/or inflammatory diseases, cardiovascular diseases, neurodegenerative diseases, allergy, asthma, pancreatitis, multiorgan failure, kidney diseases, platelet aggregation, cancer, sperm motility, graft rejection or lung injuries. Specifically, the present invention is related to substituted imino-azolinone-vinyl fused-benzene derivatives for the modulation, notably the inhibition of the activity or function of the phospho-inositide-3'OH kinase family, PI3K, particularly of PI3Kγ.

BACKGROUND OF THE INVENTION

Cellular plasma membranes can be viewed as a large store of second messenger that can be enlisted in a variety of signal transduction pathways. As regards function and regulation of effector enzymes in phospholipid signalling pathways, these enzymes generate second messengers from the membrane phospholipid pool (class I PI3 kinases (e.g. PI3Kgamma)) are dual-specific kinase enzymes, means they display both: lipid kinase (phosphorylation of phospho-inositides) as well as protein kinase activity, shown to be capable of phosphorylation of other protein as substrates, including auto-phosphorylation as intra-molecular regulatory mechanism. These enzymes of phospholipid signalling are activated in response to a variety of extra-cellular signals such as growth factors, mitogens, integrins (cell-cell interactions) hormones, cytokines, viruses and neurotransmitters such as described in Scheme 1 hereinafter and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example.

The inositol phospholipids (phosphoinositides) intracellular signalling pathway begins with binding of a signalling molecule (extra cellular ligands, stimuli, receptor dimerization, transactivation by heterologous receptor (e.g. receptor tyrosine kinase)) to a G-protein linked transmembrane receptor integrated into the plasma membrane.

PI3K converts the membrane phospholipid PIP(4,5)2 into PIP(3,4,5)3 which in turn can be further converted into another 3' phosphorylated form of phosphoinositides by 5'-specific phospho-inositide phosphatases, thus PI3K enzymatic activity results either directly or indirectly in the generation of two 3'-phosphoinositide subtypes that function as $2^{nd}$ messengers in intra-cellular signal transduction (*Trends Biochem. Sci.* 22(7) p. 267-72 (1997) by Vanhaesebroeck et al.; *Chem. Rev.* 101(8) p. 2365-80 (2001) by Leslie et al (2001); *Annu. Rev. Cell. Dev. Biol.* 17 p. 615-75 (2001) by Katso et al. and *Cell. Mol. Life Sci.* 59(5) p. 761-79 (2002) by Toker et al.). Multiple PI3K isoforms categorized by their catalytic subunits, their regulation by corresponding regulatory subunits, expression patterns and signalling-specific functions (p110α, β, δ, and γ) perform this enzymatic reaction (*Exp. Cell. Res.* 25(1) p. 239-54 (1999) by Vanhaesebroeck and Katso et al., 2001, above).

The evolutionary conserved isoforms p110α and β are ubiquitously expressed, while δ and γ are more specifically expressed in the haematopoietic cell system, smooth muscle cells, myocytes and endothelial cells (*Trends Biochem. Sci.* 22(7) p. 267-72 (1997) by Vanhaesebroeck et al.). Their expression might also be regulated in an inducible manner depending on the cellular-, tissue type and stimuli as well as disease context.

To date, eight mammalian PI3Ks have been identified, divided into three main classes (I, II, and III) on the basis of sequence homology, structure, binding partners, mode of activation, and substrate preference in vitro. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI (Vanhaesebroeck et al., 1997, above; Vanhaesebroeck et al., 1999, above and Leslie et al., 2001, above) G-protein coupled receptors mediated phosphoinositide 3'OH-kinase activation via small Glases such as Gβγ and Ras, and consequently PI3K signalling plays a central role in establishing and coordinating cell polarity and dynamic organization of the cytoskeleton—which together provides the driving force of cells to move.

Scheme 3

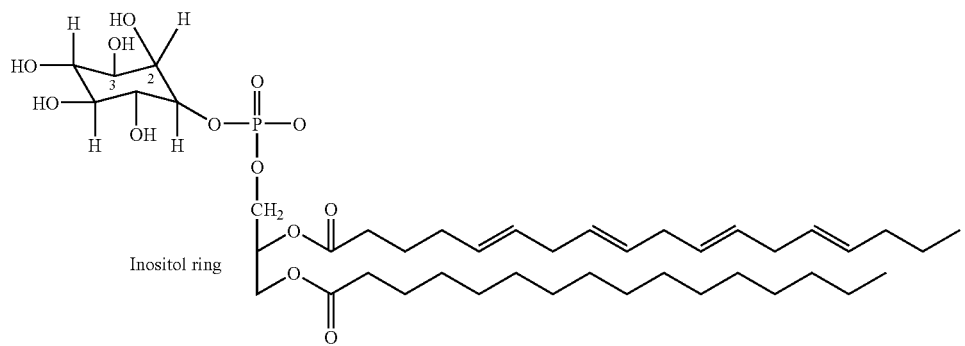

Inositol ring

PtdIns

-continued

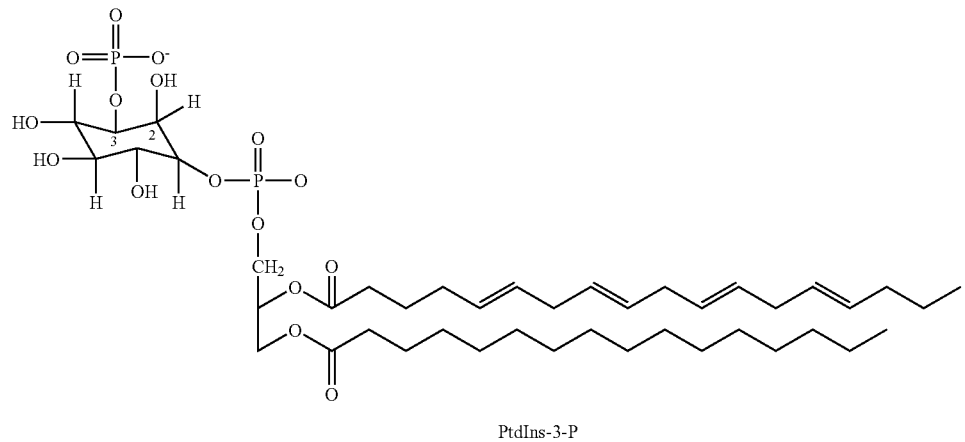

PtdIns-3-P

As above illustrated in Scheme 1, Phosphoinositide 3-kinase (PI3K) is involved in the phosphorylation of Phosphatidyliositol (PtdIns) on the third carbon of the inositol ring. The phosphorylation of PtdIns to 3,4,5-triphosphate (PtdIns(3,4, 5)P3), PtdIns(3,4)$P_2$ and PtdIns(3)P acts as second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement cell shape changes, vesicle trafficking and metabolic pathway (Katso et al., 2001, above and *Mol. Med. Today* 6(9) p. 347-57 (2000) by Stein). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (*Immunol. Today* 21(6) p. 260-4 (2000) by Wyman et al.; *Science* 287(5455) p. 1049-53 (2000) by Hirsch et al.; *FASEB J.* 15(11) p. 2019-21 (2001) by Hirsch et al. and *Nat. Immunol.* 2(2) p. 108-15 (2001) by Gerard et al.).

Recent advances using genetic approaches and pharmacological tools have provided insights into signalling and molecular pathways that mediate chemotaxis in response to chemoattractant activated G-protein coupled receptors PI3-Kinase, responsible for generating these phosphorylated signalling products, was originally identified as an activity associated with viral oncoproteins and growth factor receptor tyrosine kinases that phosphorylates phosphatidylinositol (P) and its phosphorylated derivatives at the 3'-hydroxyl of the inositol ring (Panayotou et al., *Trends Cell Biol.* 2 p. 358-60 (1992)). However, more recent biochemical studies revealed that, class I PI3 kinases (e.g. class IB isoform PI3Kγ) are dual-specific kinase enzymes, means they display both: lipid kinase (phosphorylation of phospho-inositides) as well as protein kinase activity, shown to be capable of phosphorylation of other protein as substrates, including auto-phosphorylation as intra-molecular regulatory mechanism.

PI3-kinase activation, is therefore believed to be involved in a range of cellular responses including cell growth, differentiation, and apoptosis (Parker et al., *Current Biology*, 5 p. 577-99 (1995); Yao et al., *Science*, 267 p. 2003-05 (1995)). PI3-kinase appears to be involved in a number of aspects of leukocyte activation A p85-associated PI3-kinase activity has been shown to physically associate with the cytoplasmic domain of CD28, which is an important costimulatory molecule for the activation of T-cells in response to antigen (Pages et al., *Nature*, 369 p, 327-29 (1994); Rudd, *Immunity* 4 p. 527-34 (1996)). Activation of T cells through CD28 lowers the threshold for activation by antogen and increases the magnitude and duration of the proliferative response. These effects are linked to increases in the transcription of a number of genes including interleukin-2 (IL2), an important T cell growth factor (Fraser et al., *Science,* 251 p. 313-16 (1991)). Mutation of CD28 such that it can longer interact with PI3-kinase leads to a failure to initiate IL2 production, suggesting a critical role for PI3-kinase in T cell activation. PI3Kγ has been identified as a mediator of G beta-gamma-dependent regulation of JNK activity, and G beta-gamma are subunits of heterotrimeric G proteins (Lopez-Ilasaca et al., *J. Biol. Chem.* 273(5) p. 2505-8 (1998)). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

Recently, (Laffargue et al., *Immunity* 16(3) p. 441-51 (2002)) it has been described that PI3Kγ relays inflammatory signals through various G(i)-coupled. receptors and its central to. mast cell function, stimuli in context of leukocytes, immunology includes cytokines, chemokines, adenosines, antibodies, integrins, aggregation factors, growth factors, viruses or hormones for example (*J. Cell. Sci.* 114(Pt 16) p. 2903-10 (2001) by Lawlor et al.; Laffargue et al., 2002, above and *Curr. Opinion Cell Biol.* 14(2) p. 203-13 (2002) by Stephens et al.).

Specific inhibitors against individual members of a family of enzymes provide invaluable tools for deciphering functions of each enzyme. Two compounds, LY294002 and wortmannin (cf. hereinafter), have been widely used as PI3-kinase inhibitors. These compounds are non-specific PI3K inhibitors, as they do not distinguish among the four members of Class I PI3-kinases. For example, the $IC_{50}$ values of wortmannin against each of the various Class I PI3-kinases are in the range of 1-10 nM. Similarly, the $IC_{50}$ values for LY294002 against each of these PI3-kinases is about 15-20 µM (Fruman et al., *Ann. Rev. Biochem.,* 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respirators burst involved in neutrophil destruction of invading microorganisms. Treatment of neutrophils with wortmannin prevents the fMLP-induced respiratory burst response (Thelen et al., *Proc. Natl. Acad Sci. USA*, 91 p. 4960-64 (1994)). Indeed, these experiments with wortmannin, as well as other experimental evidence, shows that PI3K activity in cells of hematopoietic lineage, particularly neutrophils, monocytes, and other types of leukocytes, is involved in many of the non-memory immune response associated with acute and chronic inflammation.

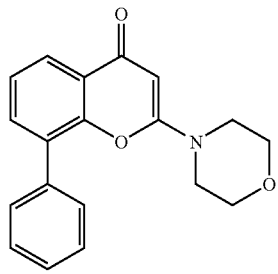

LY 294002

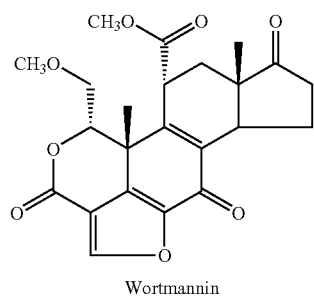

Wortmannin

Based on studies using wortmannin, there is evidence that PI3-kinase function is also required for some aspects of leukocyte signalling through G-protein coupled receptors (Thelen et al., 1994, above). Moreover, it has been shown that wortmannin and LY294002 block neutrophil migration and superoxide release. However, in as much as these compounds do not distinguish among the various isoforms of PI3K, it remains unclear which particular PI3K isoform or isoforms are involved in these phenomena. Cyclooxygenase inhibiting benzofuran derivatives are disclosed by John M. Janusz et al., in *J. Med. Chem.* 1998; Vol 41, No. 18.

SUMMARY OF THE INVENTION

The present invention relates to 2-imino-azolinone-vinyl fused-benzene derivatives of Formula (I):

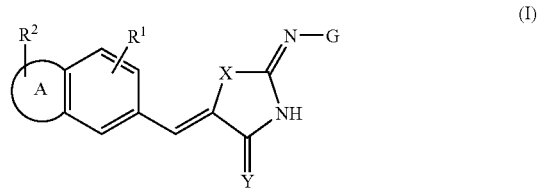

A, X, Y, R$^1$, R$^2$ and G of Formula (I) are defined in the below detailed description, their use, pharmaceutical preparation and synthesis thereof. The compounds of Formula (I) are useful as medicaments in particular for the treatment and/or prophylaxis of autoimmune disorders and/or inflammatory diseases, cardiovascular diseases, neurodegenerative diseases, kidney diseases, platelet aggregation, cancer, transplantation, graft rejection or lung injuries. According to one embodiment of the present invention, the compounds of Formula (I) are inhibitors of phosphato-inositides 3-kinases (PI3Ks), particularly of Phosphatoinositides 3-kinases gamma (PI3Kγ).

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"C$_1$-C$_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"C$_1$-C$_6$-alkyl aryl" refers to C$_1$-C$_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinoyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"C$_1$-C$_6$-alkyl heteroaryl" refers to C$_1$-C$_6$-alkyl groups having a heteroaryl substituent, including 2-furylmethyl, 2-thienylmethyl, 2-(1H-indol-3-yl)ethyl and the like.

"C$_2$-C$_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"C$_2$-C$_6$-alkenyl aryl" refers to C$_2$-C$_6$-alkenyl groups having an aryl substituent, including 2-phenylvinyl and the like.

"C$_2$-C$_6$-alkenyl heteroaryl" refers to C$_2$-C$_6$-alkenyl groups having a heteroaryl substituent, including 2-(3-pyridinyl)vinyl and the like.

"C$_2$-C$_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡H), and the like.

"C$_2$-C$_6$-alkynyl aryl" refers to C$_2$-C$_6$-alkynyl groups having an aryl substituent, including phenylethynyl and the like.

"C$_2$-C$_6$-alkynyl heteroaryl" refers to C$_2$-C$_6$-alkynyl groups having a heteroaryl substituent, including 2-thienylethynyl and the like.

"C$_3$-C$_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a C$_3$-C$_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"C$_1$-C$_6$-alkyl cycloalkyl" refers to C$_1$-C$_6$-alkyl groups having a cycloalkyl substituent, including cyclohexylmethyl, cyclopentylpropyl, and the like.

"C$_1$-C$_6$-alkyl heterocycloalkyl" refers to C$_1$-C$_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"C$_1$-C$_6$-alkyl carboxy" refers to C$_1$-C$_6$-alkyl groups having an carboxy substituent, including 2-carboxyethyl and the like.

"Acyl" refers to the group —(O)R where R includes "C$_1$-C$_6$-alkyl", "aryl", "heteroaryl", "C$_1$-C$_6$-alkyl aryl" or "C$_1$-C$_6$-alkyl heteroaryl".

"C$_1$-C$_6$-alkyl acyl" refers to C$_1$-C$_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"C$_3$-C$_8$-(hetero)cycloalkyl acyl" refers to 3 to 8 membered cycloalkyl or heterocycloalkyl groups having an acyl substituent "Acyloxy" refers to the group —OC(O)R where R includes H, "C$_1$-C$_6$-alkyl", "C$_2$-C$_6$-alkenyl", "C$_2$-C$_6$-alkynyl", "C$_3$-C$_8$-cycloalkyl", heterocycloalkyl "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-akynylheteroaryl", "C$_1$-C$_6$-alkyl cycloalkyl", "C$_1$-C$_6$-alkyl heterocycloalkyl".

"C$_1$-C$_6$-alkyl acyloxy" refers to C$_1$-C$_6$-alkyl groups having an acyloxy substituent, including 2-(acetyloxy)ethyl and the like.

"Alkoxy" refers to the group —O—R where R includes "C$_1$-C$_6$-alkyl" or "aryl" or "heteroaryl" or "C$_1$-C$_6$-alkyl aryl" or "C$_1$-C$_6$-alkyl heteroaryl". Preferred alkoxy groups include by way of example, methoxy, ethoxy, phenoxy and the like.

"C$_1$-C$_6$-alkyl alkoxy" refers to C$_1$-C$_6$-alkyl groups having an alkoxy substituent, including 2-ethoxyethyl and the like.

"Alkoxycarbonyl" refers to the group —C(O)OR where R includes H, "C$_1$-C$_6$-alkyl" or "aryl" or "heteroaryl" or "C$_1$-C$_6$-alkyl aryl" or "C$_1$-C$_6$-alkyl heteroaryl".

"C$_1$-C$_6$-alkyl alkoxycarbonyl" refers to C$_1$-C$_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or C$_1$-C$_6$-alkyl or aryl or heteroaryl or "C$_1$-C$_6$-alkyl aryl" or "C$_1$-C$_6$-alkyl heteroaryl".

"C$_1$-C$_6$-alkyl aminocarbonyl" refers to C$_1$-C$_6$-alkyl groups having an aminocarbonyl substituent, including 2-(dimethylaminocarbonyl)ethyl and the like.

"Acylamino" refers to the group —NRC(O)R' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocloalkyl", "aryl", "heteroaryl", "C$_1$-C$_6$-alkyl aryl" or "C$_1$-C$_6$-alkyl heteroaryl", "C$_{2-6}$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl acylamino" refers to C$_1$-C$_6$-alkyl groups having an acylamino substituent, including 2-(propionylamino) ethyl and the like.

"Ureido" refers to the group —NRC(O)NR'R" where each R, R', R" is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl", and where R' and R", together with the nitrogen atom to which they are attached, can optionally form a 3-8-membered heterocycloalkyl ring.

"C$_1$-C$_6$-alkyl ureido" refers to C$_1$-C$_6$-alkyl groups having an ureido substituent, including 2-(N'-methylureido)ethyl and the like.

"Carbamate" refers to the group —NRC(O)OR' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_1$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"Amino" refers to the group —NRR' where each R,R' is independently hydrogen or "C$_1$-C$_6$-alkyl" or "aryl" or "heteroaryl" or "C$_1$-C$_6$-alkyl aryl" or "C$_1$-C$_6$-alkyl heteroaryl", or "cycloalkyl", or "heterocycloalkyl", and where R and R', together with the nitrogen atom to which they are attached, can optionally form a 3-8-membered heterocycloalkyl ring.

"C$_1$-C$_6$-alkyl amino" refers to C$_1$-C$_5$-alkyl groups having an amino substituent, including 2-(1-pyrrolidinyl)ethyl and the like.

"Ammonium" refers to a positively charged group —N$^+$RR'R", where each R,R',R" is independently "C$_1$-C$_6$-alkyl" or "C$_1$-C$_6$-alkyl aryl" or "C$_1$-C$_6$-alkyl heteroaryl", or "cycloalkyl", or "heterocycloalkyl", and where R and R', together with the nitrogen atom to which they are attached, can optionally form a 3-8-membered heterocycloalkyl ring.

"C$_1$-C$_6$-alkyl ammonium" refers to C$_1$-C$_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —SO$_2$—R wherein R is selected from H, "C$_1$-C$_6$-alkyl", "C$_1$-C$_6$-alkyl" substituted with halogens, e.g. an —OSO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-allyl cycloalkyl", "C$_1$-C$_6$-alkyl heterocycloalkyl".

"C$_1$-C$_6$-alkyl sulfonyloxy" refers to C$_1$-C$_5$-alkyl groups having a sulfonyloxy substituent, including 2-(methylsulfonyloxy)ethyl and the like. "Sulfonyl" refers to group "—SO$_2$—R" wherein R is selected from H, "aryl", "heteroaryl", "C$_1$-C$_6$-alkyl", "C$_1$-C$_6$-alkyl" substituted with halogens, e.g., an —SO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_1$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyl" refers to C$_1$-C$_5$-alkyl groups having a sulfonyl substituent, including 2-(methylsulfonyl)ethyl and the like.

"Sulfinyl" refers to a group "—S(O)—R" wherein R is selected from H, "C$_1$-C$_6$-alkyl", "C$_1$-C$_6$-alkyl" substituted with halogens, e.g., a —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfinyl" refers to C$_1$-C$_5$-alkyl groups having a sulfinyl substituent, including 2-(methylsulfinyl)ethyl and the like.

"Sulfanyl" refers to groups —S—R where R includes H, "C$_1$-C$_6$-alkyl", "C$_1$-C$_6$-alkyl" substituted with halogens, e.g., a —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl". Preferred sulfanyl groups include methylsulfanyl, ethylsulfanyl, and the like. "C$_1$-C$_6$-alkyl sulfanyl" refers to C$_1$-C$_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonylamino" refers to C$_1$-C$_5$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl aminosulfonyl" refers to C$_1$-C$_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "C$_1$-C$_6$-alkyl aryl", "C$_1$-C$_6$-alkyl heteroaryl", "C$_1$-C$_6$-alkyl cycloalkyl", "C$_1$-C$_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, meglumine (N-methylglucamine), benethamine (N-benzylphenethylamine), diethylamine, piperazine, thromethamine (2-amino-2-hydroxymethyl-1,3-propanediol), procaine as well as amines of formula —NR,R',R" wherein R, R', R" is independently hydrogen, alkyl or benzyl. Especially preferred salts are sodium and potassium salts.

"Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR,R',R"+Z$^-$, wherein R, R', R" is independently hydrogen, alkyl, or benzyl, C$_1$-C$_6$-alkyl, C$_2$-C$_6$-alkenyl, C$_2$-C$_6$-alkynyl, C$_1$-C$_6$-alkyl aryl, C$_1$-C$_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein. "Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

It has now been found that compounds of the present invention are modulators of the Phosphatoinositides 3-kinases (PI3Ks), particularly of Phosphatoinositides 3-kinase γ (PI3Kγ). When the phosphatoinositides 3-kinase (PI3K) enzyme is inhibited by the compounds of the present invention, PI3K is unable to exert its enzymatic, biological and/or pharmacological effects. The compounds of the present invention are therefore useful in the treatment and prevention of autoimmune disorders and/or inflammatory diseases, cardiovascular diseases, neurodegenerative diseases, bacterial or viral infections, kidney diseases, platelet aggregation, cancer, transplantation, graft rejection or lung injuries.

The present invention relates to 2-imino-azolinone-vinyl fused-benzene derivatives of Formula (I):

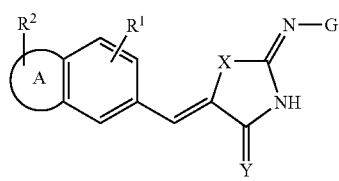

wherein A; X; Y; R$^1$; R$^2$ and G are defined below and with the proviso that the following 8 compounds are excluded:

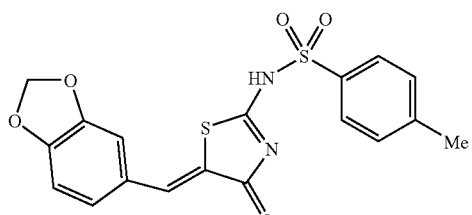

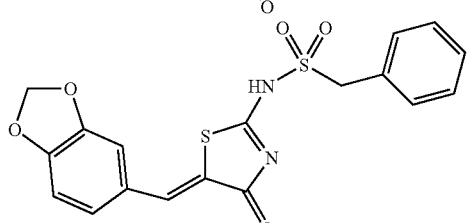

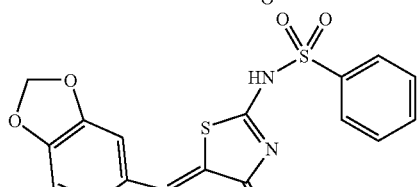

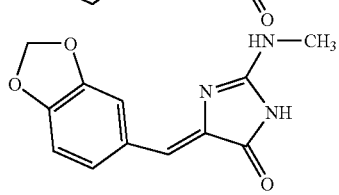

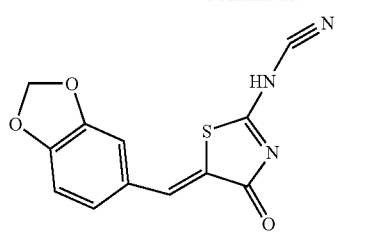

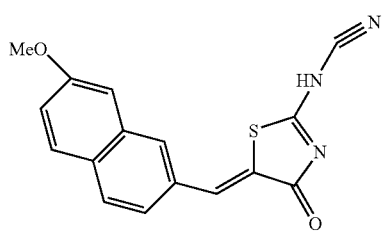

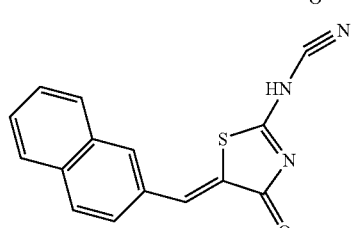

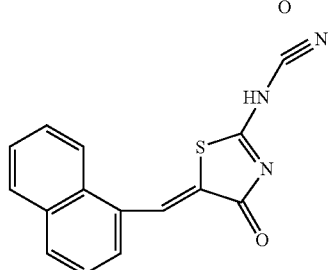

The present invention further relates to the use of 2-imino-azolinone-vinyl fused-benzene derivatives of Formula (I):

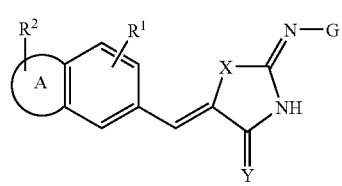

wherein A; X; Y; R$^1$; R$^2$; and G are defined below as a medicament and with the proviso that the following 4 compounds are excluded:

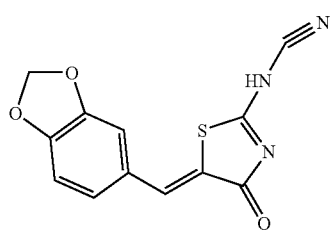

-continued

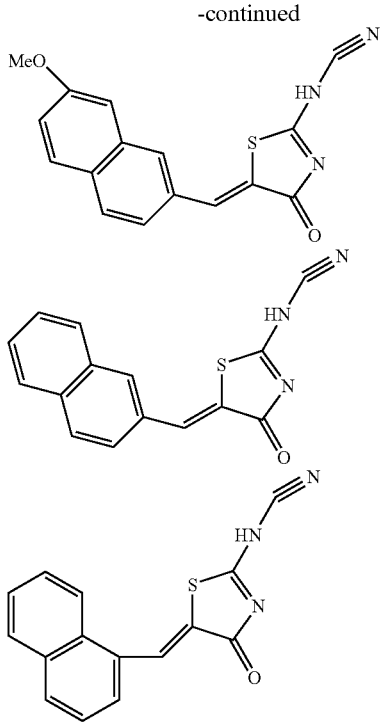

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

A first aspect of the present invention consists in novel compounds of Formula (I):

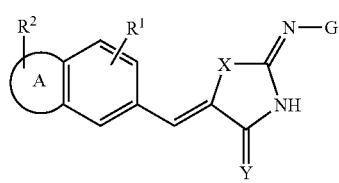

A is an unsubstituted or substituted 5-8 membered heterocyclic group or an unsubstituted or substituted carbocyclic group. Preferably, A is a heterocyclic moiety.

Said carbocyclic group may be fused with an unsubstituted or substituted aryl, an unsubstituted or substituted heteroaryl, an unsubstituted or substituted cycloalkyl or an unsubstituted or substituted heterocycloalkyl.

Such heterocyclic or carbocyclic groups comprise aryl, heteroaryl, cycloalkyl and heterocycloalkyl, including phenyl, phenantrenyl, cyclopentyl, cyclohexyl, norbornyl, pyrrolidine, piperidine, piperazine, 1-methylpiperazine, morpholine, pyrrolyl, furanyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5- oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

Further examplary heterocyclic or carbocyclic groups A include unsubstituted or substituted dioxolenyl, unsubstituted or substituted dioxinyl, unsubstituted or substituted dihydrofuranyl, unsubstituted or substituted (dihydro)furanyl, unsubstituted or substituted (dihydro)oxazinyl, unsubstituted or substituted oxazinoyl, unsubstituted or substituted pyridinyl, unsubstituted or substituted isooxazolyl, unsubstituted or substituted oxazolyl unsubstituted or substituted (dihydro)napthalenyl, unsubstituted or substituted pyrimidinyl, unsubstituted or substituted triazolyl, unsubstituted or substituted imidazolyl, unsubstituted or substituted pyrazinyl, unsubstituted or substituted thiazolyl, unsubstituted or substituted thiadiazolyl, unsubstituted or substituted oxadiazolyl.

In one embodiment of the present invention A is a dioxolenyl, a pyrazinyl or a pyridinyl moiety, preferably a dioxolenyl or a pyridinyl moiety.

X is S, O or $-NR^3$, preferably S. $R^3$ is selected from the group comprising or consisting of H or optionally substituted $C_1$-$C_6$-alkyl.

Y is S or O, preferably O.

$R^1$ is selected from the group comprising or consisting of H, CN, carboxy, acyl, optionally substituted $C_1$-$C_6$-alkoxy, halogen, hydroxy, acyloxy, an unsubstituted or substituted $C_1$-$C_6$-alkyl carboxy, an unsubstituted or substituted $C_1$-$C_6$-alkyl acyloxy, an unsubstituted or substituted $C_1$-$C_6$-alkyl alkoxy, alkoxycarbonyl, an unsubstituted or substituted $C_1$-$C_6$-alkyl alkoxycarbonyl, aminocarbonyl, an unsubstituted or substituted $C_1$-$C_6$-alkyl aminocarbonyl, acylamino, an unsubstituted or substituted $C_1$-$C_6$-alkyl acylamino, ureido, an unsubstituted or substituted $C_1$-$C_6$-alkyl ureido, amino, an unsubstituted or substituted $C_1$-$C_6$-alkyl amino, ammonium, sulfonyloxy, an unsubstituted or substituted $C_1$-$C_6$-alkyl sulfonyloxy, sulfonyl, an unsubstituted or substituted $C_1$-$C_6$-alkyl sulfonyl, sulfinyl, an unsubstituted or substituted $C_1$-$C_6$-alkyl sulfinyl, sulfanyl, an unsubstituted or substituted $C_1$-$C_6$-alkyl sulfanyl, sulfonylamino, an unsubstituted or substituted $C_1$-$C_6$-alkyl sulfonylamino or carbamate. Preferably $R^1$ is H.

$R^2$ is selected from the group comprising or consisting of H, halogen, acyl, amino, an unsubstituted or substituted $C_1$-$C_6$-alkyl, an unsubstituted or substituted $C_2$-$C_6$-alkenyl, an unsubstituted or substituted $C_2$-$C_6$-alkynyl, an unsubstituted or substituted $C_1$-$C_6$-alkyl carboxy, an unsubstituted or substituted $C_1$-$C_6$-alkyl acyl, an unsubstituted or substituted $C_1$-$C_6$-alkyl alkoxycarbonyl, an unsubstituted or substituted $C_1$-$C_6$-alkyl aminocarbonyl, an unsubstituted or substituted $C_1$-$C_6$-alkyl acyloxy, an unsubstituted or substituted $C_1$-$C_6$-alkyl acylamino, an unsubstituted or substituted $C_1$-$C_6$-alkyl ureido, an unsubstituted or substituted $C_1$-$C_6$-alkyl carbamate, an unsubstituted or substituted $C_1$-$C_6$-alkyl amino, an unsubstituted or substituted $C_1$-$C_6$-alkyl alkoxy, an unsubstituted or substituted $C_1$-$C_6$-alkyl sulfanyl, an unsubstituted or substituted $C_1$-$C_6$-alkyl sulfinyl, an unsubstituted or substituted $C_1$-$C_6$-alkyl sulfonyl, an unsubstituted or substituted $C_1$-$C_6$-alkyl sulfonylaminoaryl, aryl, heteroaryl, an unsubstituted or substituted $C_3$-$C_8$-cycloalkyl or heterocycloalkyl, an unsubstituted or substituted $C_1$-$C_6$-alkyl aryl, an unsubstituted or substituted $C_1$-$C_6$-alkyl heteroaryl, an unsubstituted or substituted $C_2$-$C_6$-alkenyl-aryl or -heteroaryl, an unsubstituted or substituted $C_2$-$C_6$-alkynyl aryl or -heteroaryl, carboxy, cyano, hydroxy, $C_1$-$C_6$-alkoxy, nitro, acylamino, ureido, sulfonylamino, sulfanyl, or sulfonyl. Preferably $R^2$ is H.

In a specific embodiment, $R^1$ and $R^2$ are both H.

G is a substituted or unsubstituted $C_1$-$C_6$-alkyl, substituted or unsubstituted $C_2$-$C_6$-alkyenyl, substituted or unsubstituted $C_2$-$C_6$-alkynyl, substituted or unsubstituted heteroaryl, an unsubstituted or substituted $C_1$-$C_6$-alkyl aryl, an unsubstituted or substituted $C_1$-$C_6$-alkyl heteroaryl, an unsubstituted or substituted $C_2$-$C_6$-alkenyl-aryl or -heteroaryl, an unsubstituted or substituted $C_2$-$C_6$-alkynyl aryl or -heteroaryl, substituted or unsubstituted $C_1$-$C_6$-alkoxy, cyano, substituted or unsubstituted $C_1$-$C_6$-acyl or G is a sulfonyl moiety.

In a preferred embodiment, G is selected from substituted or unsubstituted $C_1$-$C_6$-alkoxy, cyano, or a substituted or unsubstituted sulfonyl moiety.

In another preferred embodiment, G is selected from substituted or unsubstituted $C_1$-$C_6$-alkyl, including propyl and methyl; $C_2$-$C_6$-alkenyl; $C_2$-$C_6$-alkynyl and $C_1$-$C_6$-alkyl aryl, including phenyl methyl.

In particular, G is selected from the group comprising or consisting of an optionally substituted sulfonyl moiety, including phenyl sulfonyl, 4-methylphenyl sulfonyl, methyl sulfonyl, ethyl sulfonyl, 6-chloropyridine-3-sulfonyl, thiophene-2-carboxylic acid methyl ester-3-sulfonyl, 5-chloro-1,3-dimethyl-1H-pyrazole-4 sulfonyl, 3-chlorophenyl sulfonyl, 2-chlorophenyl sulfonyl, quinoline-8-sulfonyl, biphenyl-2-sulfonyl, pyridine-3-sulfonyl; a cyano group or an substituted or unsubstituted $C_1$-$C_6$-alkoxy, including methoxy.

In a catalog from Ambinter, 3 library compounds of Formula (I) are disclosed:

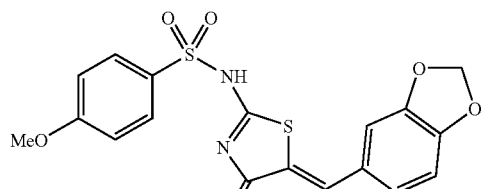

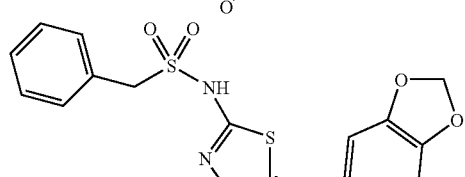

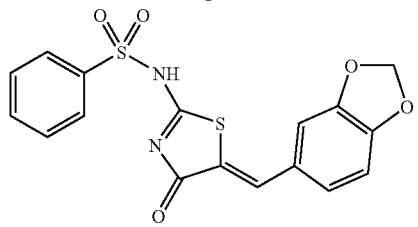

The compounds are tautomers of Formula (I). No biological activity is disclosed for said 3 compounds.

The following tautomer of compounds of Formula (I) is disclosed in Roué et al., 1999, *Tetrahedron* 55, 14729-14738 and is an isomer of Leucettmine B2, a marine natural product derived from sponge. No biological activity is disclosed for said isomer.

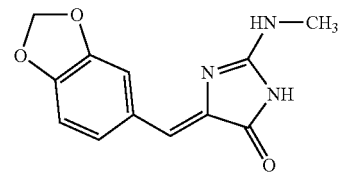

The following tautomers of compounds of Formula (I) are disclosed in EP 0697410 and are said to be useful as prophylactic or therapeutic agents for the treatment of complications of chronic diabetes.

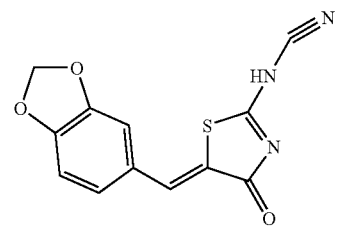

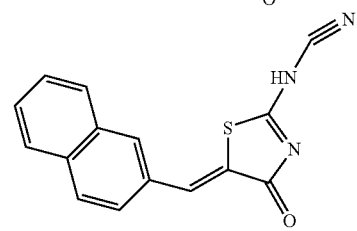

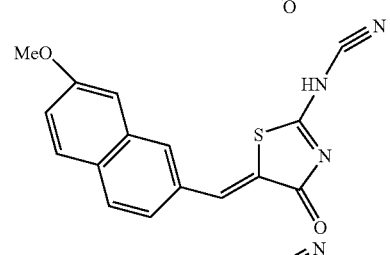

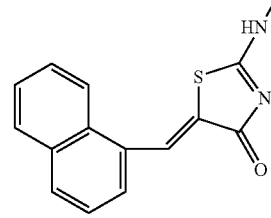

In one embodiment of the present invention G is a sulfonyl moiety of the formula —$SO_2$—$R^4$, whereby $R^4$ is selected from the group comprising or consisting of H; unsubstituted or substituted $C_1$-$C_6$-alkyl, including methyl and ethyl; unsubstituted or substituted $C_2$-$C_6$-alkenyl; unsubstituted or substituted $C_2$-$C_6$-alkynyl; unsubstituted or substituted $C_1$-$C_6$-alkyl carboxy; an unsubstituted or substituted $C_1$-$C_6$-alkyl acyl; an unsubstituted or substituted $C_1$-$C_6$-alkyl alkoxycarbonyl; an unsubstituted or substituted $C_1$-$C_6$-alkyl aminocarbonyl; an unsubstituted or substituted $C_1$-$C_6$-alkyl acyloxy; an unsubstituted or substituted $C_1$-$C_6$-alkyl acylamino; an unsubstituted or substituted $C_1$-$C_6$-alkyl ureido; an unsubstituted or substituted $C_1$-$C_6$-alkyl carbamate; an unsubstituted or substituted $C_1$-$C_6$-alkyl amino; an unsubstituted or substituted $C_1$-$C_6$-alkyl alkoxy; an unsubstituted or substituted $C_1$-$C_6$-alkyl sulfanyl; an unsubstituted or substituted $C_1$-$C_6$-alkyl sulfinyl; an unsubstituted or substituted $C_1$-$C_6$-alkyl sulfonyl; an unsubstituted or substituted $C_1$-$C_6$-alkyl sulfonylaminoaryl; aryl, including phenyl, methyl phenyl, biphenyl and chloro phenyl; heteroaryl, including pyridinyl, thiophene-2-carboxylic acid methyl ester-3-yl, quinolinyl, 5-chloro-1,3-dimethyl-1H-pyrazolyl; an unsubstituted or substituted $C_3$-$C_8$-cycloalkyl or heterocycloalkyl; an unsubstituted or substituted $C_1$-$C_6$-alkyl aryl; an unsubstituted or substituted $C_1$-$C_6$-alkyl heteroaryl; an unsubstituted or substituted $C_2$-$C_6$-alkenyl-aryl or -heteroaryl; an unsubstituted or substituted $C_2$-$C_6$-alkynyl aryl or -heteroaryl; carboxy; hydroxy; $C_1$-$C_6$-alkoxy; acylamino; sulfonylamino.

In one embodiment of the present invention $R^4$ is an unsubstituted or substituted aryl, an unsubstituted or substituted heteroaryl, an unsubstituted or substituted $C_1$-$C_3$ alkyl.

In a specific embodiment, X is S, Y is O, $R^1$ and $R^2$ are H, A is selected from a dioxolenyl, a pyridinyl or a pyrazinyl moiety, preferably a dioxolenyl or a pyridinyl moiety.

The compounds according to Formula (I) are suitable for the modulation, notably the inhibition of the activity of phosphatoinositides 3-kinases (PI3K), particularly phosphatoinositides 3-kinase (PI3Kγ). It is therefore believed that the compounds of the present invention are also particularly useful for the treatment and/or prevention of disorders which are mediated by PI3Ks, particularly PI3Kγ. Said treatment involves the modulation—notably the inhibition or the down regulation—of the phosphatoinositides 3-kinases.

The compounds of the present invention may be obtained as E/Z isomer mixture or as essentially pure E-isomers or Z isomers. The E/Z isomerism preferably refers to the vinyl moiety linking the phenyl with the azolidinone moiety. In a specific embodiment, the compounds of Formula (I) are Z-isomers.

Compounds of the present invention of for use in the present invention include in particular those of the group consisting of:

| Example | Name |
|---|---|
| 1 | N-(5-Benzo[1,3]dioxol-5-ylmethylene-4-oxo-thiazolidin-2-ylidene)-2-chloro-benzenesulfonamide; |
| 2 | Ethanesulfonic acid(5-benzo[1,3]dioxol-5-ylmethylene-4-oxo-thiazolidin-2-ylidene)-amide; |
| 3 | N-(5-Benzo[1,3]dioxol-5-ylmethylene-4-oxo-thiazolidin-2-ylidene)-3-chloro-benzenesulfonamide; |
| 4 | 5-Chloro-1,3-dimethyl-1H-pyrazole-4-sulfonic acid(5-benzo[1,3]dioxol-5-ylmethylene-4-oxo-thiazolidin-2-ylidene)-amide; |
| 5 | 3-(5-Benzo[1,3]dioxol-5-ylmethylene-4-oxo-thiazolidin-2-ylidenesulfamoyl)-thiophene-2-carboxylic acid methyl ester; |
| 6 | 6-Chloro-pyridine-3-sulfonic acid(5-benzo[1,3]dioxol-5-ylmethylene-4-oxo-thiazolidin-2-ylidene)-amide; |
| 7 | Quinoline-8-sulfonic acid(5-benzo[1,3]dioxol-5-ylmethylene-4-oxo-thiazolidin-2-ylidene)-amide; |
| 8 | N-(5-Benzo[1,3]dioxol-5-ylmethylene-4-oxo-thiazolidin-2-ylidene)-benzene sulfonamide; |
| 9 | N-(5-Benzo[1,3]dioxol-5-ylmethylene-4-oxo-thiazolidin-2-ylidene)-4-methyl-benzenesulfonamide; |
| 10 | N-(5-Benzo[1,3]dioxol-5-ylmethylene-4-oxo-thiazolidin-2-ylidene)-methane sulfonamide; |
| 11 | N-[5-(2,2-Difluoro-benzo[1,3]dioxol-5-ylmethylene)-4-oxo-thiazolidin-2-ylidene]-benzenesulfonamide; |
| 12 | N-[5-(2,2-Difluoro-benzo[1,3]dioxol-5-ylmethylene)-4-oxo-thiazolidin-2-ylidene]-4-methyl-benzenesulfonamide; |
| 13 | N-[5-(2,2-Difluoro-benzo[1,3]dioxol-5-ylmethylene)-4-oxo-thiazolidin-2-ylidene]-methanesulfonamide; |
| 14 | Biphenyl-2-sulfonic acid(5-benzo[1,3]dioxol-5-ylmethylene-4-oxo-thiazolidin-2-ylidene)-amide |
| 15 | Pyridine-3-sulfonic acid(5-benzo[1,3]dioxol-5-ylmethylene-4-oxo-thiazolidin-2-ylidene)-amide; |
| 16 | 3-(4-Oxo-5-quinolin-6-ylmethylene-thiazolidin-2-ylidenesulfamoyl)-thiophene-2-carboxylic acid methyl ester; |
| 17 | 2-Chloro-N-(4-oxo-5-quinolin-6-ylmethylene-thiazolidin-2-ylidene)-benzene sulfonamide; |
| 18 | 3-(5-Benzo[1,3]dioxol-5-ylmethylene-4-oxo-thiazolidin-2-ylidenesulfamoyl)-thiophene-2-carboxylic acid; |
| 19 | 5-Benzo[1,3]dioxol-5-ylmethylene-4-oxo-thiazolidin-2-ylidene-cyanamide; |
| 20 | 5-Benzo[1,3]dioxol-5-ylmethylene-thiazolidine-2,4-dione 2-(O-methyl-oxime); |
| 21 | 4-Oxo-5-quinoxalin-6-ylmethylene-thiazolidin-2-ylidene-cyanamide; |
| 22 | 5-Benzo[1,3]dioxol-5-ylmethylene-2-benzylimino-thiazolidin-4-one; |
| 23 | 2-Benzylimino-5-quinolin-6-ylmethylene-thiazolidin-4-one; |
| 24 | 2-Propylimino-5-quinolin-6-ylmethylene-thiazolidin-4-one; |
| 25 | 5-Benzo[1,3]dioxol-5-ylmethylene-2-propylimino-thiazolidin-4-one; |
| 26 | 5-(4-Dimethylamino-quinazolin-6-ylmethylene)-2-methylamino-thiazol-4-one. |

The compounds of the present invention are useful as medicaments. They may be used for the preparation of a medicament for the prophylaxis and/or treatment of autoimmune disorders and/or inflammatory diseases, cardiovascular diseases, neurodegenerative diseases, kidney diseases, platelet aggregation, cancer, transplantation, graft rejection or lung injuries.

Especially, the compounds of the present invention may be used for the preparation of a medicament for the prophylaxis and/or treatment of a disorder selected from multiple sclerosis, psoriasis, rheumatoid arthritis, systemic lupus erythematosis, inflammatory bowel disease, lung inflammation, thrombosis or brain infection/inflammation such as meningitis or encephalitis, Alzheimer's disease, Huntington's disease, CNS trauma, stroke or ischemic conditions, cardiovascular diseases such as athero-sclerosis, heart hypertrophy, cardiac myocyte dysfunction, elevated blood pressure or vasoconstriction.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including multiple sclerosis, Alzheimer's disease, Huntington's disease, CNS trauma, stroke or ischemic conditions.

In still a further embodiment according to the invention, the compounds of Formula (I) are useful for the treatment and/or prophylaxis of cardiovascular diseases such as athero-sclerosis, heart hypertrophy, cardiac myocyte dysfunction, elevated blood pressure or vasoconstriction.

In still another embodiment according to the invention, the compounds of Formula (I) are useful for the treatment and/or prophylaxis of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In still another embodiment, the invention provides a method of treatment of a disorder selected from autoimmune disorders and/or inflammatory diseases, cardiovascular diseases, neurodegenerative diseases, kidney diseases, platelet aggregation, cancer, transplantation, graft rejection or lung injuries, comprising the step of administering a compound according to the invention to a patient in need thereof.

Still a further object of the present invention is a process for preparing 2-imino-azolinone-vinyl fused-benzene derivatives according to Formula (I).

The 2-imino-azolinone-vinyl fused-benzene derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

Methods of Preparing the Compounds within Formula (I).

Generally, the 2-imino-azolinone-vinyl fused-benzene derivatives according to the general Formula (I) could be obtained by several synthetic approaches, using both solution-phase and solid-phase chemistry protocols (Brummond et al., *J.O.C.*, 64, 1723-1726 (1999)), either by conventional methods or by microwave-assisted techniques (see schemes 1, 2 and 3).

In a first step, approximately equimolar amounts of the reactant P1 and reagent P2 (2-amino-4,5-dihydro-1,3-thiazol-4-one, 2-Imino-thiazolidine-4-thione, 2-Imino-oxazolidin-4-one, 2-Imino-oxazolidine-4-thione, 2-imino-1-alkyl-imidazolidin-4-one or 2-Imino-1-alkyl-imidazolidine-4-thione) or reagent P3 (Oxazolidine-2,4-dithione, 2-Thioxo-oxazolidin-4-one, 1-Alkyl-2-thioxo-imidazolidin-4-one, 1-Alkyl-imidazolidine-2,4-dithione, Thiazolidine-2,4-dithione or rhodanin) are heated in the presence of a mild base to provide the corresponding olefin of Formula (Ia) or (Ib) respectively.

2-imino-azolinone-vinyl fused-benzene derivatives can be obtained by reacting intermediate (Ia) with sulfonylhalides or acylhalides (L-G, L=leaving group) in the presence of a scavenger base affording compounds of Formula (I) as described in Scheme 1 below.

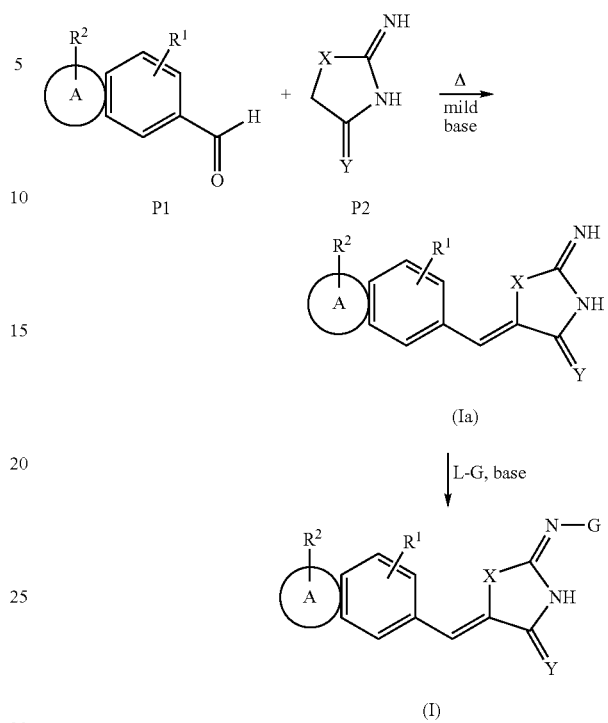

In case G is alkyl or aryl, the 2-imino-azolinone-vinyl fused-benzene derivatives of Formula (I) can be accessed through the reaction of intermediate (Ib) with the corresponding amines, as set out in Scheme 2 below.

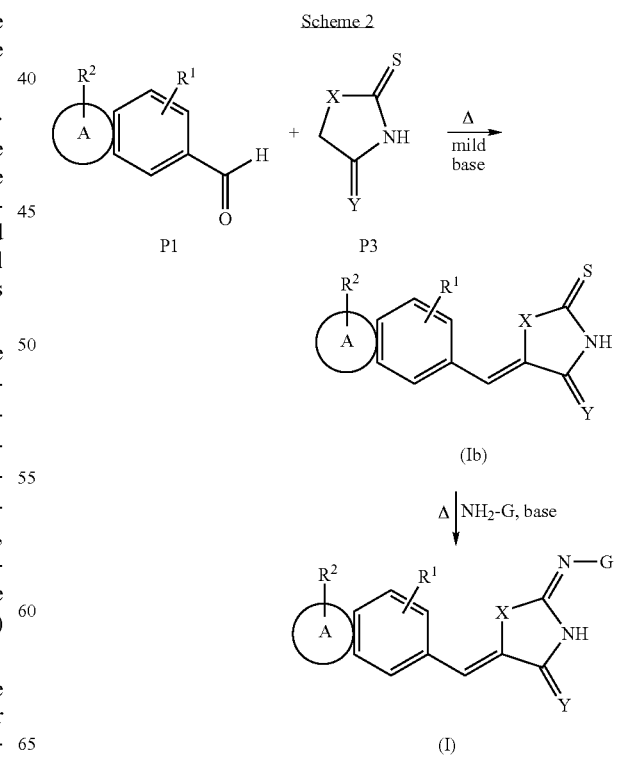

While the first step leading to intermediates (Ia) and (Ib) may be carried out in the absence of a solvent at a temperature, which is sufficiently high to cause at least partial melting of the reaction mixture, it is preferably carried out in the presence of a reaction inert solvent. A preferred such temperature is in the range of from 100° C. to 250° C., and especially preferred is a temperature of from 120° C. to 200° C. Examples of such solvents for the above reaction include solvents like dimethoxymethane, xylene, toluene, o-dichlorobenzene etc. Examples of suitable mild bases for the above reaction are alkali metal and alkaline earth salts of week acids such as the ($C_1$-$C_{12}$)-alkyl carboxylic acids and benzoic acid, alkali metal and alkaline earth carbonates and bicarbonates such as calcium carbonate, magnesium carbonate, potassium bicarbonate and secondary amines such as piperidine, morpholine as well as tertiary amines such as pyridine, triethylamine, diisopropylethylamine, N-methylmorpholine, N-Ethylpiperidine, N-Methylpiperidine and the like. Especially preferred mild bases are sodium acetate or piperidine for reasons of economy and efficiency.

In a typical such reaction (Tietze et al., in "*The Knoevenagel reaction*", p. 341 ff., Pergamon Press, Oxford 1991, Eds.: Trost B. M., Fleming I.) the aldehyde starting material P1 and the corresponding heterocycle P2 (2-amino-4,5-dihydro-1,3-thiazol-4-one, 2-Imino-thiazolidine-4-thione, 2-Imino-oxazolidin-4-one, 2-Imino-oxazolidine-4-thione, 2-Imino-1-alkyl-imidazolidin-4-one or 2-Imino-1-alkyl-imidazolidine-4-thione) or heterocycle P3 (Oxazolidine-2,4-dithione, 2-Thioxo-oxazolidin-4-one, 1-Alkyl-2-thioxo-imidazolidin-4-one, 1-Alkyl-imidazolidine-2,4-dithione, Thiazolidine-2,4-dithione or rhodanin) are combined in approximately equimolar amounts with 0.5 to one equivalent of piperidine in dimethoxymethane or similar solvent and heated between 120 and 200° C. at which the reaction is substantially complete in from 15 minutes to 3 hours. The desired olefins of Formula (Ia) or (Ib) respectively are then isolated by filtration, in case they precipitated out of the reaction mixture upon cooling, or for example, by mixing with water and subsequent filtration, to obtain the crude products, which are purified, if desired, e.g. by crystallization or by standard chromatographic methods.

Alternatively olefins of Formula (Ia) or (Ib) respectively may be obtained typically by mixing equimolar amounts of P2 (2-amino-4,5-dihydro-1,3-thiazolone, 2-Imino-thiazolidine-4-thione, 2-Imino-oxazolidin-4-one, 2-Imino-oxazolidine-4-thione, 2-Imino-1-alkyl-imidazolidin-4-one or 2-Imino-1-alkyl-imidazolidine-4-thione) or heterocycle P3 respectively (Oxazolidine-2,4-dithione, 2-Thioxo-oxazolidin-4-one, 1-Alkyl-2-thioxo-imidazolidin-4-one, 1-Alkyl-imidazolidine-2,4-dithione, Thiazolidine-2,4-dithione or rhodanin) with aldheyde P1 and molar excess, preferably a 2 to 4 fold excess, of anhydrous sodium acetate and the mixture is heated at a temperature high enough to effect melting, at which temperature the reaction is mainly complete in from 5 to 60 minutes.

More preferred reactions conditions are where the above reactions are carried out in acidic media such as acetic acid in the presence of sodium acetate, α-amino-acids or β-alanine. 2-amino-4,5-dihydro-1,3-thiazol-4-one (P2) or rhodanin (P3) are mixed with equimolar amounts of aldehyde P1 in the presence of β-alanine in the range of 0.1 to 1 equivalent in acetic acid. The reaction mixture is heated between 80° to 130° C. for 5 minutes to 5 hours, affording the intermediates (Ia) and (Ib) as precipitates. Filtration and washing with water afford compounds in high purity.

Above described reactions can be carried out alternatively under microwave conditions as heating source between 140° C. and 240° C. at which the reaction is substantially complete from 3 to 10 minutes.

In case G is substituted or un-substituted alkyl- or arylsulfonyl group or substituted or un-substituted alkyl- or arylcarbonyl group conditions, as shown on Scheme 1 are applied. Typically intermediate (Ia) is dissolved in an aprotic solvent such as NMP or DMA. This solution is treated with at least one equivalent, preferably two to three equivalents of tertiary amine such as pyridine, triethylamine, diisopropylethylamine, N-methyl morpholine, N-Ethylpiperidine, N-Methylpiperidine and the like. Especially, preferred bases are triethylamine or diisopropylethylamine, followed by the addition of the corresponding sulfonyl- or acylchloride at reaction temperatures between 0° to 50° C. Typically the reaction mixtures are stirred between 0.5 to 15 hours, upon which the solvent is evaporated and the final 2-imino-azolinone-vinyl fused-benzene derivatives are precipitated using water and ethylacetate. Standard chromatography techniques may be applied to reach required purities.

In case G is a substituted or un-substituted alkyl or arylgroup, the 2-imino-azolinone-vinyl fused-benzene derivatives of Formula (I) can be accessed through the reaction of intermediate (Ib) with the corresponding substituted or un-substituted alkyl- or arylamines. Intermediates (Ib) are reacted with 1 to 10 equivalents of the corresponding amines in the presence of an inorganic base in reaction solvents like MeOH, EtOH, Acetonitrile, DME and the like. Preferably the solvent is mixed with up to 50% of water. Preferred inorganic bases are $K_2CO_3$, $CaCO_3$, $Na_2CO_3$, $BaCO_3$ and the like. Typical reaction times are 3 to 15 hours under solvent reflux. Typically 2-imino-azolinone-vinyl fused-benzene derivatives of this type precipitate out of the reaction mixture. In some cases additional water maybe needed for precipitation in order to afford compounds of Formula (I) in high purity and quantity.

In case G is a cyano-group, substituted or un-substituted oxime-ether reaction Scheme 3 below is applied to afford 2-imino-azolinone-vinyl fused-benzene derivatives. Intermediate (b) is methylated affording intermediate (Ic), which is ultimately transformed into compounds of Formula (I) using the corresponding carbodiimide.

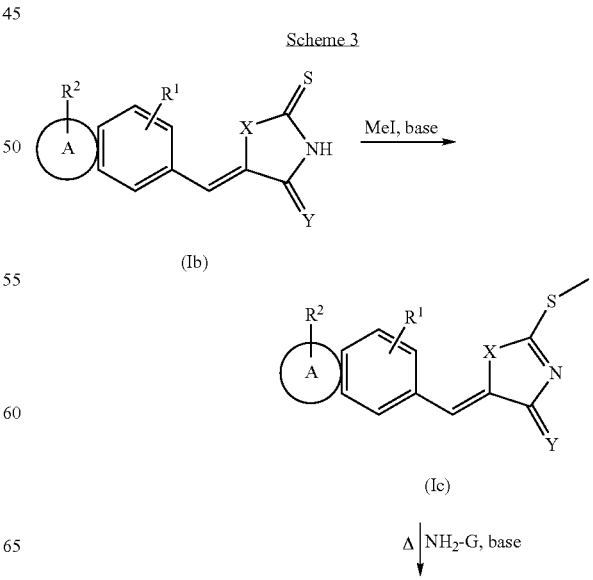

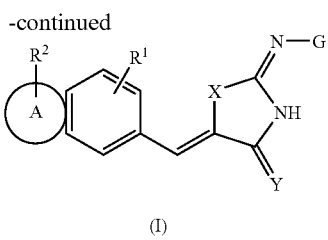

Typically methylation of intermediate (Ib) takes place in the presence of base such as pyridine, triethylamine, diisopropylethylamine, N-methylmorpholine, N-ethylpiperidine, N-methylpiperidine and the like and an alkylating agent such methyliodide, dimethylsulfate or the like in an inert solvent, which remains unaffected by the presence of alkylating agents. The reaction mixture may be stirred at 25° C. to 60° C., preferably at room temperature between 0.5 to 15 hours. Most preferred conditions are the use of methyliodide in the presence of Hünig's base in tetrahydrofuran or dioxane. Excess of reagents may be easily removed after completion by applying a vacuum to the reaction. Compounds of Formula (Ic) easily precipitate upon adding of water.

In a typical reaction where the S-alkyl group of compounds of Formula (Ic) is replaced by a $NH_2$-G moiety leading to compounds of Formula (I) the intermediates (Ic) are treated with a strong base such potassium-tert.butoxide, potassiumhydride, sodiumhydride, preferably with potassium tert.butoxide in an inert solvent, which remains unaffected by the presence of a strong base. The mixture is subsequently treated with the corresponding nucleophile, such as cyanamide, substituted or unsubstituted oxime-ether, hydroxylamine and heated between 50 and 150° C., preferably at 80° C. for 1 to 15 hours. Excess of reagents may be removed by standard washing procedures, where upon the compounds of Formula (I) precipitate.

If the above set of general synthetic methods are not applicable to obtain compounds according to Formula (I) and/or to necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing 2-iminoazolinone-vinyl fused-benzene derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient Typical unit dosage forms include prefilled, premeasured ampoules or syringes of the liquid compositions or pills, tablets, capsules or the like in the case of solid compositions. In such compositions, the 2-iminoazolinone-vinyl fused-benzene derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as pepper-mint, methyl salicylate, or orange flavouring.

Injectable compositions are typically based upon injectable sterile saline or phosphate-buffered saline or other injectable carriers known in the art. As above mentioned, the 2-iminoazolinone-vinyl fused-benzene derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20th Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples, which are not construed to be viewed as limiting the scope of the invention. The following abbreviations are hereinafter used in the accompanying examples:

Å (Angstrom), eq. (equivalents), min (minute), h (hour), g (gram), mg (milligam),), mm (millimeter), mmol (millimole), m.p. (melting point), nm (nanometer), mL (milliliter), μL (microliters), mM (millimolar), MHz (Megahertz), ACN (acetonitrile), ATP (Adenoside Triphosphate), Boc (butoxycarbonyl), BSA (Bovine Serum Albumin), Cbz (carboxybenzyl), CDCl$_3$ (deuterated chloroform), cHex (cyclohexane), dba (dibenzylidene acetone), DCM (dichloromethane), DEAD (diethylazodicarboxylate, DIBALH (Diisobutylaluminum Hydride), DIC (diisopropylcarbodiimide), DIEA (diisopropyl ethylamine), DMAP (4-dimethylaminopyridine), DME (dimethoxyethane), DMEM (Dulbecco's Modified Eagle Medium), DMF (dimethylformamide), DMSO (dimethyl sulfoxide), DMSO-d$_6$ (deuterated dimethylsulfoxide), DTT (1,4-Dithio-D,L-threitol), EDC (1-(3-dimethylaminopropyl)-3-ethylcarbodiimide hydrochloride), EDTA (ethylenediamine tetraacetic acid), EtOAc (ethylacetate), Et$_2$O (diethylether), Fmoc (9-fluorenylmethoxy-carbonyl), HOBt (1-hydroxybenzotriazole), HPLC (High Performance Liquid Chromatography), K$_2$CO$_3$ (potassium carbonate), LC (Liquid Chromatography), MgSO$_4$ (magnesium sulfate), MS (mass spectrometry), MsCl (methylsulfonylchloride), MTBE (tert-butylmethylether), NaH (sodium hydride), NaHCO$_3$ (sodium bicarbonate), nBuLi (n-butyllithium), NMP (N-Methyl-2-Pyrrolidone), PBS (Phosphate Buffered Saline), PCC pyridinium chloro chromate), PE (petroleum ether), PI3K (Phosphoinositide 3-kinase), PVT (polyvinyl toluene), QCl (tetrabutylammonium chloride), RT (room temperature), SPA (Scintillation Proximity Assay), TBTU (O-benzotriazolyl-N,N,N',N'-tetramethyluronium-tetrafluoro borate), TEA (triethylamine), TFA (trifluoroacetic acid), THF (tetrahydrofiran), TLC (Thin Layer Chromatography), TMOF (trimethyl orthoformate), TMAD (N,N,N',N'-tetramethylazodicarboxamide), TosCl (toluenesulfonyl chloride).

EXAMPLES

The following intermediate commercially available aldehydes were used:

Piperonal, 6-Quinolinecarboxaldehyde, 6-Quinoxalinecarboxaldehyde, 2,2-Difiuoro-1,3-benzodioxole-5-carboxaldehyde.

The following intermediates were prepared:

Intermediate 1

Preparation of 4-N-dimethvlaminoguinazoline-6-carboxaldehyde

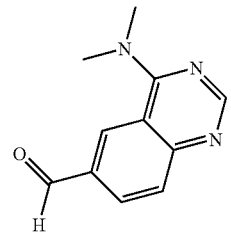

Step I: 4-Nitro isophthalic acid

A mixture of 3-methyl-4-nitrobenzoic acid (150 g, 0.825 mol), pyridine (1.5 L) and water (1.5 L) was heated to reflux. To the hot reaction mixture was added KMnO$_4$ (10 mol) portion wise and reflux for 72 h The hot reaction mixture was filtered through celite and washed with hot water. The filtrate was concentrated under vacuum, residue diluted with water (750 mL) and acidified with concentrated HCl at 0° C. The solid obtained was filtered, washed with water and dried under vacuum to give 4-nitro isophthalic acid (98 g, 56%).

TLC, Chloroform/Methanol, 7:3, R$_f$=0.2.

Step II: 4-Amino isophthalic acid

To a solution of 4-nitro isophthalic acid (98 g, 0.457 mol) in methanol (5 L) was added Pd/C (20%) and hydrogenated at RT for 4 h. The reaction mixture was filtered through celite and filtrate concentrated under vacuum to give 4-amino isophthalic acid (72 g, 87%) as a solid.

TLC, Chloroform/Methanol, 7:3, R$_f$=0.4.

Step III: 4-Oxo-3,4-dihydroquinazolin-6-carboxylic acid

A mixture of 4-amino isophthalic acid (17 g, 0.093 mol) and formamide (85 mL) was heated at 180° C. for 5 h. The reaction mixture was cooled to RT and added acetone. The solid precipitate thus obtained was stirred for 2 h, filtered and dried to give 4-oxo-3,4-dihydroquinazoline-6-carboxylic acid (11 g, 61%).

TLC, Chloroform/Methanol, 8:2, R$_f$=0.25.

Step IV: 4-Oxo-3,4-dihydroquinazoline-6-methyl carboxylate

To a solution of 4-oxo-3,4-dihydroquinazoline-6-carboxylic acid (24 g, 0.126 mol) in dry methanol (800 mL) was added thionylchloride (37 g) at 5° C. and then refluxed at 80° C. for 5 h. The reaction mixture was concentrated under vacuum and crude taken in ethylacetate (250 mL). The organic layer was washed with 10% aqueous NaHCO$_3$, water, brine and dried. The solvent was removed under vacuum to give 4-oxo-3,4-dihydroquinazoline-6-methyl carboxylate (24 g, 92%) as a solid.

TLC, Chloroform/Methanol, 8:2, R$_f$=0.6

Step V: Methyl-4-chloroquinazoline-6-carboxylate

A mixture of 4-oxo-3,4-dihydroquinazolin-6-methyl carboxylate (12 g, 0.058 mol) and phosphorylchloride (180 mL) was heated to reflux for 7 h. Excess phosphorylchloride was distilled off and crude taken in ethyl cetate (250 mL). The organic layer was washed with 10% aqueous $NaHCO_3$ solution, water, brine and dried. The solvent was removed under vacuum and crude purified by column chromatography over silica gel (30% ethylacetate in pet. ether) to give methyl-4-chloroquinazoline-6-carboxylate (4.5 g, 34%) as a solid.

TLC, pet. ether/EtOAc, 1:1, $R_f$=0.65.

Step VI: 4-Chloroquinazoline-6-yl methanol

To a solution of methyl-4-chloroquinazoline-6-carboxylate (3.5 g, 0.015 mol) in dry THF (35 mL) at −25° C. was added DIBAL-H (4.4 g, 0.031 mol) and stirred at −25° C. to RT for 2 h. The reaction mixture was cooled to −10° C. and quenched with 10% aqueous $NaHCO_3$ (9 mL). The reaction mixture was extracted with ethylacetate (100 mL), washed with water, brine and dried. The solvent was removed under vacuum to give 4-chloroquinazoline-6-yl methanol (2 g, 66%).

TLC, Chloroform/Methanol, 8:2, $R_f$=0.35.

Step VII: 4-Chloroquinazoline-6-carboxaldehyde

To a solution of 4-chloroquinazoline-6yl methanol (3.5 g, 0.018 mol) in dry $CH_2Cl_2$ (100 mL) was added Dess-Martin periodinane (8.4 g, 0.019 mol) and stirred at RT for 30 min. The reaction mixture was washed with 10% aqueous $NaHCO_3$ (75 mL), water, brine and dried. The solvent was removed under vacuum to give 4-chloroquinazoline-6-carboxaldehyde (3 g, 88%) as pale yellow solid.

TLC, Chloroform/Methanol, 9:1, $R_f$=0.6.

Step VIII: 4-N-dimethylaminoquinazoline-6-carboxaldehyde

In a flask of 100 ml 4-chloroquinazoline-6-carboxaldehyde (200 mg, 1 mmol) was dissolved in dioxane (15 ml). To this solution was added an aqueous solution of dimethylamine (585 mg, 5 mmol) in 12 ml water, and the yellow mixture was stirred for two hours at room temperature. After evaporating the solvents in vacuo a yellow solid was obtained (190 mg, yield: 91%) which was used without further purification.

HPLC: 0.82 min. LC-MS: M/Z ESI: 1.02 min, 202.12 (M+1). NMR: $^1$H NMR (DMSO-d6) δ 10.08 (s, 1H), 8.75 (s, 1H), 8.53 (s, 1H), 8.10 (d, J=9 Hz, 1H), 7.78 (d, J=9 Hz, 1H), 3.41 (s, 6H).

Intermediate 2

Preparation of 5-Benzo[1,3]dioxol-5-ylmethylene-2-imino-thiazolidin-4-one

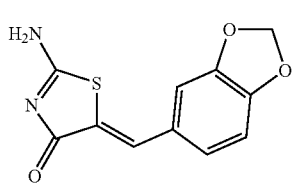

In a 100 ml round bottom flask were placed 3.87 g of pseudohydantoine, 5 g of piperonal and 1.92 g of beta-alanine in 30 ml of acetic acid The reaction was stirred for 3 h at 100° C. and then slowly cooled to room temperature, while the desired condensation product crystallized. The crystals were filtered and washed with acetic acid (RT) affording 8.0 g of pure 5-Benzo[1,3]dioxol-5-ylmethylene-2-imino-thiazolidin-4-one.

HPLC: 2.29 min. LC-MS: M/Z ESI: 1.24 min, 249.12 (M+1). NMR: $^1$H NMR (DMSO-d6) δ9.35 (br. s, 1H), 9.09 (br s, 1H), 7.52 (s, 1H), 7.04-7.13 (m, 3H), 6.13 (s, 2H).

The following intermediates were synthesized according to the synthesis of intermediate 2 using suitable starting materials.

Intermediate 3

Preparation of 2-Amino-5-(2,2-difluoro-benzo[1,3]dioxol-5-ylmethylene)-thiazol-4-one

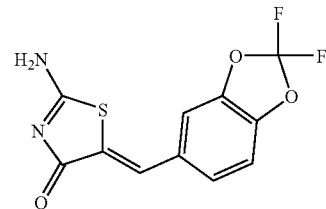

HPLC: 3.02 min. LC-MS: M/Z ESI: 1.53 min, 285.12 (M+1). NMR: $^1$H NMR (DMSO-d6) δ9.48 (br. s, 1H), 9.22 (br s, 1H), 7.44-7.61 (m, 3H), 7.41 (d, J=3 Hz, 1H).

Intermediate 4

Preparation of 2-Imino-5-quinolin-6-ylmethylene-thiazolidin-4-one

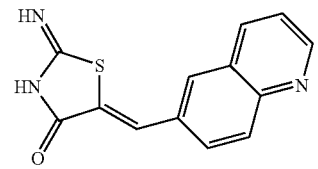

HPLC: 1.19 min. LC-MS: M/Z ESI: 1.16 min, 256.14 (M+1). NMR: $^1$H NMR (DMSO-d6) δ9.50 (br. s, 1H), 9.24 (br s, 1H), 8.94 (dd, J=6.1; 1.7 Hz, 1H), 8.42 (d, J=7.5 Hz, 1H), 8.18 (d, J=1.86 Hz, 1H), 8.11 (d, J=8.6 Hz, 1H), 7.92 (dd, J=6.1, 1.7 Hz, 1H), 7.76 (s, 1H), 7.59 (dd, J=4.1, 8.3 Hz, 1H).

Intermediate 5

Preparation of 5-(4-Dimethylamino-quinazolin-6-ylmethylene)-2-thioxo-thiazolidin-4-one

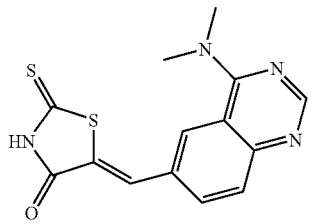

HPLC: 1.97 min. LC-MS: M/Z ESI: 1.23 min, 317.10 (M+1). NMR: $^1$H NMR (DMSO-d6) δ14.25 (br. s, 1H), 8.80 (s, 1H), 8.55 (s, 1H), 8.12 (d, J=8.7 Hz, 1H), 7.92 (m, 2H).

Intermediate 6

Preparation of 5-Quinolin-6-ylmethylene-2-thioxo-thiazolidin-4-one

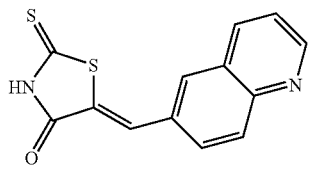

HPLC: 2.11 min. LC-MS: M/Z ESI: 1.23 min, 273.10 (M+1). NMR: $^1$H NMR(DMSO-d6) δ 13.9 (s, b 1H), 8.97 (dd, J=1.9 Hz, 4.1 Hz, 1H), 8.52 (d, J=7.9 Hz, 1H), 8.23 (s, 1H), 8.11 (d, J=9.0 Hz, 1H), 7.96 (dd, J=1.9 Hz, 4.1 Hz, 1H), 7.79 (s, 1H), 7.61 (dd, J=4.1 Hz, 8.3 Hz, 1H).

Intermediate 7

Preparation of 5-Benzo[1,3]dioxol-5-ylmethylene-2-thioxo-thiazolidin-4-one

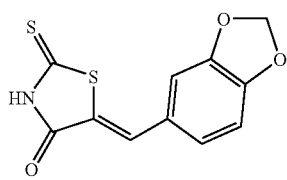

HPLC: 3.55 min. LC-MS: M/Z ESI: 1.33 min, 266.12 (M−1). NMR: $^1$H NMR (DMSO-d6) δ12.5 (br. s, 1H), 7.73 (s, 1H), 7.06-7.18 (m, 3H), 6.05 (s, 2H).

Intermediate 8

Preparation of 5-Quinoxaline-6-ylmethylene-2-thioxo-thiazolidin-4-one

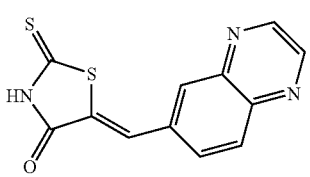

HPLC: 3.01 min. LC-MS: M/Z ESI: 1.17 min, 272.10 (M−1). NMR: $^1$H NMR (DMSO-d6) δ 14.0 (br. s, 1H), 9.00 (s, 2H), 8.31 (s, 1H), 8.21 (d, J=8.7 Hz, 1H), 8.05 (d, J=8.7 Hz, 1H), 7.90 (s, 1H).

Intermediate 9

5-Benzo[1,3]dioxol-5-ylmethylene-2-methylsulfanyl-thiazol-4-one

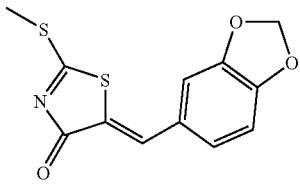

2 g (7.54 mmol) of 5-Benzo[1,3]dioxol-5-ylmethylene-2-thioxo-thiazolidin-4-one and 1.5 ml (1.15 eq.) of DIEA were dissolved in 80 ml NMP. To this solution was added dropwise a freshly prepared solution of 2.43 ml (5 eq.) of Methyliodide in 10 ml NMP. The reaction mixture was stirred for two hours at RT. EtOAc was added and the organic layer was washed 5 times with brine and twice with water. The organic layer was reduced to 50% of volume, where upon 5-Benzo[1,3]dioxol-5-ylmethylene-2-methylsulfanyl-thiazol-4-one started to crystallize. Crystals were filtered off and washed with cold EtOAc.

Yield=1.5 g (71%). HPLC: 3.44 min. LC-MS: M/Z ESI: 1.68 min, 280.19 (M+1). NMR: $^1$H NMR (DMSO-d6) δ7.76 (s, 1H), 7.09-7.26 (m, 3H), 6.14 (s, 2H), 2.82 (s, 3H).

The following intermediates were synthesized according to the preparation of intermediate 9 using suitable staring materials.

Intermediate 10

Preparation of 2-Methylsulfanyl-5-quinoxalin-6-ylmethylene-thiazol-4-one

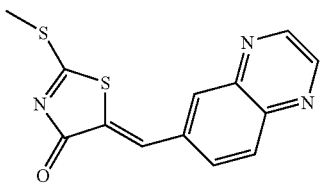

HPLC: 3.32 min. LC-MS: M/Z ESI: 1.20 min, 286.10 (M−1). NMR: $^1$H NMR (DMSO-d6) δ 9.01 (s, 2H), 8.31 (s, 1H), 8.21 (d, J=8.7 Hz, 1H), 8.05 (d, J=8.7 Hz, 1H), 7.90 (s, 1H), 2.85 (s, 3H).

Intermediate 11

Preparation of 2-Methylsulfanyl-5-quinolin-6-ylmethylene-thiazol-4-one

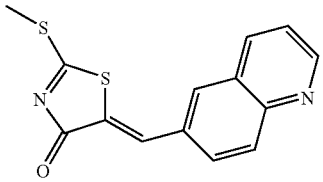

HPLC: 2.00 min. LC-MS: M/Z ESI: 1.48 min, 287.10 (M+1). NMR: $^1$H(NMR DMSO-d6) δ 8.97 (m, 1H), 8.50 (s, 1H), 8.12 (d, J=8.7 Hz, 1H), 7.97-8.01 (m, 2H), 7.64 (dd, J=4.1 Hz, 8.3 Hz, 1H), 2.86 (s, 3H).

The following examples were synthesized:

Example 1

Preparation of N-(5-Benzo[1,3]dioxol-5-ylmethylene-4-oxo-thiazolidin-2-ylidene-2-chloro-benzene-sulfonamide

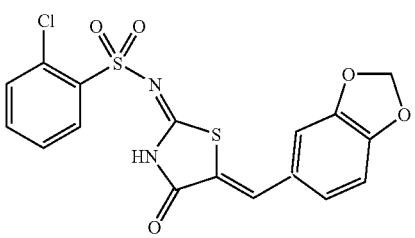

5-Benzo[1,3]dioxol-5-ylmethylene-2-imino-thiazolidin-4-one (100 mg, 0.4 mmol) were dissolved in 3 ml NMP, followed by diisopropylethylamine (250 µl) and 2-chlorobenzene-sulfonylchloride. After 8 hours the reaction was complete. Ethylacetate was added and the organic layer was washed with brine and dried over MgSO4. The crude was purified on Parallex Flex. Yield=33.0 mg (17%). HPLC: 3.92 min. LC-MS: M/Z ESI: 1.49 min, 421.06 (M−1). NMR: $^1$H NMR (DMSO-d6) δ 13.1 (b s, 1H), 8.12 (d, J=9 Hz, 1H), 7.69-7.72 (m, 3H), 7.61 (m, 1H), 7.16-7.21 (m, 2H), 7.13 (d, J=9 Hz, 1H), 6.15 (s, 2H).

The following compounds were synthesized according to the synthesis of Example 1 using suitable aldehydes such as e.g. piperonal, 6-quinolinecarboxaldehyde, 6-quinoxalinecarboxaldehyde, 2,2-difluoro-1,3-benzodioxole-5-carboxaldehyde:

Example 2

Preparation of ethanesulfonic acid (5-benzo[1,3]dioxol-5-ylmethylene-4-oxo-thiazolidin-2-ylidene-amide

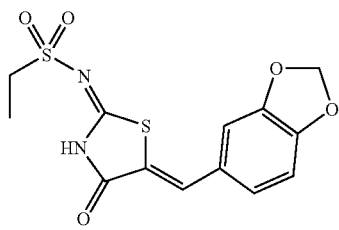

Yield=50.0 mg (37%). HPLC: 3.04 min. LC-MS: M/Z ESI: 1.49 min, 339.16 (M−1).

Example 3

Preparation of N-(5-Benzo[1,3]dioxol-5-ylmethyleneoxo-thiazolidin-2-yliden-3-chloro-benzene-sulfonamide

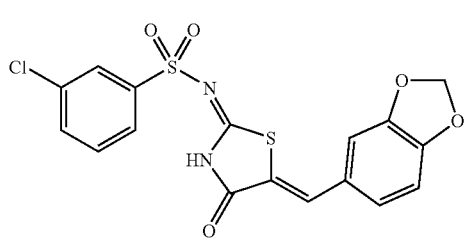

Yield=30.0 mg (16%). HPLC: 4.15 min. LC-MS: M/Z ESI: 1.54 min, 421.15 (M−1).

Example 4

Preparation of 5-Chloro-1.3-dimethyl-1H-pyrazole-4-sulfonic acid (5-benzo[1,3]dioxol-5-ylmethyl-eneoxo-thiazolidin-2-ylidene)-amide

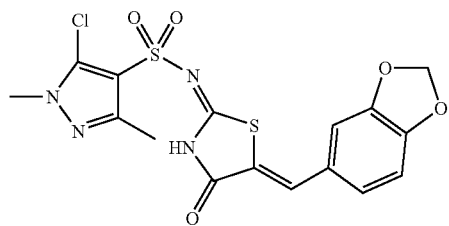

Yield=41.0 mg (23%). HPLC: 3.58 min. LC-MS: M/Z ESI: 1.35 min, 439.05 (M−1).

Example 5

Preparation of 3-(5-Benzo[1,3]dioxol-5-ylmethyl-ene-4-oxo-thiazolidin-2-ylidenesulfamoyl)-thiophene-2-carboxylic acid methyl ester

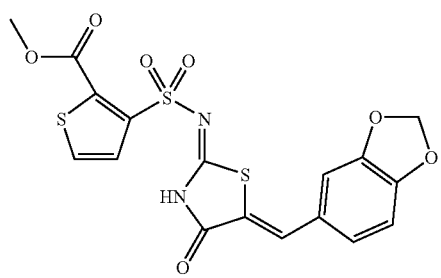

Yield=46.0 mg (25%). HPLC: 3.66 min. LC-MS: M/Z ESI: 1.38 min, 439.05 (M−1). NMR: $^1$H NMR (DMSO-d6) δ 13.0 (b s, 1H), 8.0 (d, J=3 Hz, 1H), 7.74 (s, 1H), 7.59 (d, J=3 Hz, 1H), 7.13-7.24 (m, 3H), 6.15 (s, 2H), 3.82 (s, 3H).

Example 6

Preparation of 6-Chloro-pyridine-3-sulfonic acid (5-benzo[1,3]dioxol-5-ylmethylene-4-oxo-thiazolidin-2-ylidene)-amide

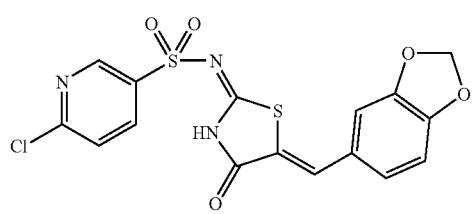

Yield=21.0 mg (13%). HPLC: 3.78 min. LC-MS: M/Z ESI: 1.46 min, 422.05 (M−1).

Example 7

Preparation of Quinoline-8-sulfonic acid (5-benzo[1,3]dioxol-5-ylmethylene-4-oxo-thiazolidin-2-ylidene)-amide

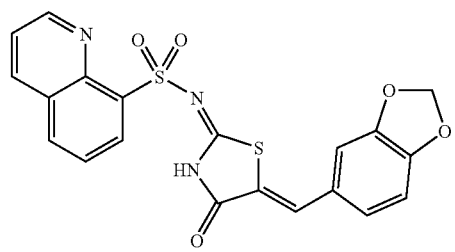

Yield=27.0 mg (15%). HPLC: 3.59 min. LC-MS: M/Z ESI: 1.38 min, 438.04 (M−1).

Example 8

Preparation of N-(5-Benzo[1,3]dioxol-5-ylmethyl-ene-4-oxo-thiazolidin-2-ylidene)-benzenesulfonamide

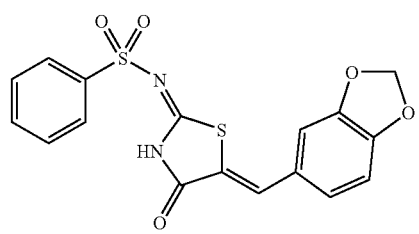

Yield=80.0 mg (51%). HPLC: 3.82 min. LC-MS: M/Z ESI: 1.42 min, 387.11 (M−1). NMR: $^1$H NMR (DMSO-d6) δ 13.5 (b s, 1H), 7.89 (m, 2H), 7.60-7.65 (m, 4H), 7.15-7.20 (m, 3H), 6.15 (s, 2H).

Example 9

Preparation of N-(5-Benzo[1,3]dioxol-5-ylmethyl-ene-4-oxo-thiazolidin-2-ylidene)-4-methyl-benzene-sulfonamide

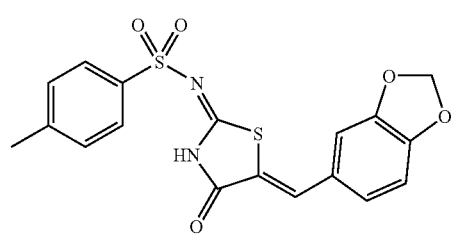

Yield=90.0 mg (52%). HPLC: 4.00 min. LC-MS: M/Z ESI: 1.51 min, 401.11 (M−1).

Example 10

Preparation of N-(5-Benzo[1,3]dioxol-5-ylmethylene-4-oxo-thiazolidin-2-ylidene)-methanesulfonamide

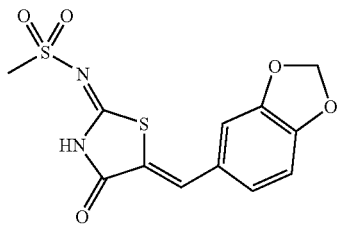

Yield=16.0 mg (13%). HPLC: 2.85 min. LC-MS: M/Z ESI: 1.17 min, 325.06 (M−1).

Example 11

Preparation of N-[5-(2,2-Difluoro-benzo[1,3]dioxol-5-ylmethylene)-4-oxo-thiazolidin-2-ylidene]-benzenesulfonamide

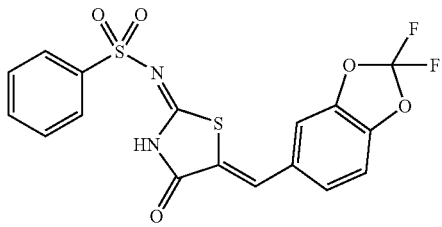

Yield=91.0 mg (54%). BPLC: 4.33 min. LC-MS: M/Z ESI: 1.66 min, 423.24 (M−1). NMR: $^1$H NMR (DMSO-d6) δ 13.2 (b s, 1H), 7.28-7.93 (m, 9H).

Example 12

Preparation of N-[5-(2,2-Difluoro-benzo[1,3]dioxol-5-ylmethylene)-4-oxo-thiazolidin-2-ylidene]-4-methyl-benzenesulfonamide

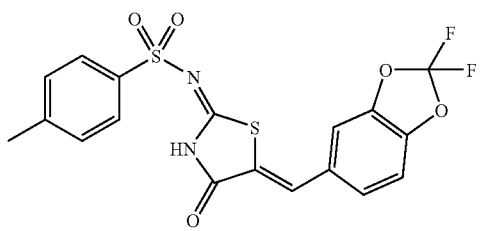

Yield=90.0 mg (53%). HPLC: 4.52 min. LC-MS: M/Z ESI: 1.65 min, 437.23 (M−1). NMR: $^1$H NMR (DMSO-d6) δ 12.6 (b s, 1H), 7.30-7.96 (m, 8H), 2.15 (s, 3H).

Example 13

Preparation of N-[5-(2,2-Difluoro-benzo[1,3]dioxol-5-ylmethylene)-4-oxo-thiazolidin-2-ylidene]-methanesulfonamide

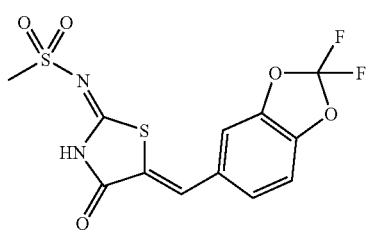

Yield=18.0 mg (12%). HPLC: 3.55 min. LC-MS: M/Z ESI: 1.39 min, 361.16 (M−1). NMR: $^1$H NMR (DMSO-d6) δ 12.9 (b s, 1H), 7.43-7.96 (m, 4H), 3.15 (s, 3H).

Example 14

Preparation of Biphenyl-2-sulfonic acid (5-benzo[1,3]dioxol-5-ylmethylene-4-oxo-thiazolidin-2-ylidene)-amide

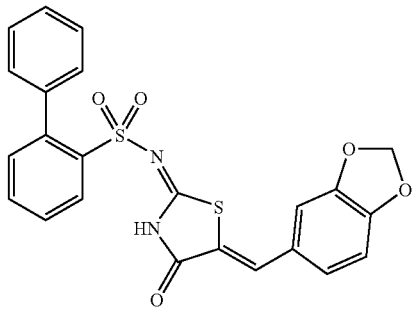

Yield=28.0 mg (15%). HPLC: 4.27 min LC-MS: M/Z ESI: 1.70 min, 463.12 (M−1). NMR: ¹H NMR (DMSO-d6) δ 12.6 (b s, 1H), 7.97 (d, J=6 Hz, 1H), 7.44-7.55 (m, 3H), 6.91-7.16 (m, 9H), 5.98 (s, 2H).

Example 15

Preparation of Pyridine-3-sulfonic acid (5-benzo[1,3]dioxol-5-ylmethylene-4-oxo-thiazolidin-2-ylidene)-amide

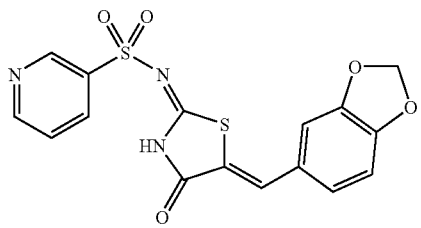

Yield=56.0 mg (36%). HPLC: 3.22 min. LC-MS: M/Z ESI: 1.30 min, 388.12 (M−1). NMR. ¹H NMR (DMSO-d6) δ 9.08 (s, 1H), 8.90 (d, 1H), 8.31 (d, J=8.2 Hz, 1H), 7.62-7.81 (m, 2H), 7.10-7.30 (m, 3H), 6.16 (s, 2H).

Example 16

Preparation of 3-(4-Oxo-5-quinolin-6-ylmethylene-thiazolidin-2-ylidenesulfamoyl)-thiophene-2-carboxylic acid methyl ester

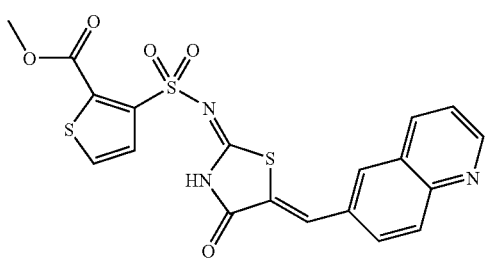

Yield=137.0 mg. (74%). HPLC: 2.46.pin. LC-MS: M/Z ESI: 1.33 min, 458.12 (M−1). NMR: ¹H NMR (DMSO-d6) δ 9.06 (s, 1H), 8.55 (d, J=8.2 Hz, 1H), 8.30 (s, 1H), 8.20 (d, J=8.2 Hz, 1H), 8.03 (m, 3H), 7.62-7.70 (m, 2H), 3.80 (s, 3H).

Example 17

Preparation of 2-Chloro-N-(4-oxo-5-quinolin-6-ylmethylene-thiazolidin-2-ylidene)-benzenesulfonamide

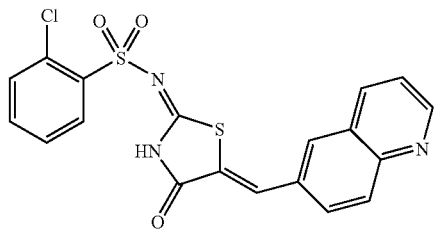

Yield=60.0 mg (35%). HPLC: 2.74 min. LC-MS: M/Z ESI: 1.40 min, 428.09 (M−1). NMR: ¹H NMR (DMSO-d6) δ 9.00 (s, 1H), 8.55 (d, J=8.2 Hz, 1H), 8.32 (s, 1H), 8.00-8.20 (m, 4H), 8.03 (m, 3H), 7.50-7.72 (m, 4H).

Example 18

Preparation of 3-(5-Benzo[1,3]dioxol-5-ylmethylene-4-oxo-thiazolidin-2-ylidenesulfamoyl)-thiophene-2-carboxylic acid

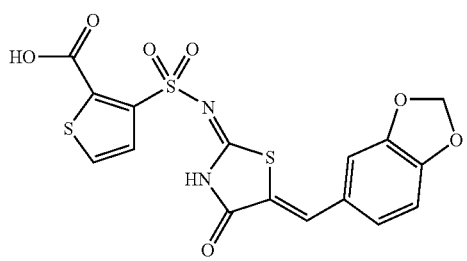

35 mg (0.08 mmol) of 3-(5-Benzo[1,3]dioxol-5-ylmethylene-4-oxo-thiazolidin-2-ylidenesulfamoyl)-thiophene-2-carboxylic acid methyl ester (Example 5) were dissolved in THF/water. 6 mg of LiOH.H₂O were added, and the reaction was followed by TLC. After complete saponification the reaction medium was acidified to pH 3.5, where upon the desired compound precipitated. Washing and drying afforded 25 mg (70%) of 3-(5-Benzo[1,3]dioxol-5-ylmethylene-4-oxo-thiazolidin-2-ylidenesulfamoyl)-thiophene-2-carboxylic acid.

HPLC: 3.20 min. LC-MS: M/Z ESI: 1.05 min, 393.09 (M−1). NMR: $^1$H NMR (DMSO-d6) δ 13.2 (b s, 2H), 7.94 (d, J=3 Hz, 1H), 7.71 (s, 1H), 7.55 (d, J=3 Hz, 1H), 7.13-7.19 (m, 3H), 6.14 (s, 2H).

Example 19

Preparation of 5-Benzo[1,3]dioxol-5-ylmethylene-4-oxo-thiazolidin-2-ylidene-cyanamide

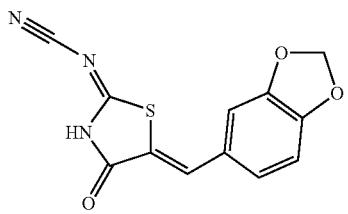

200 mg (0.72 mmol) of 5-Benzo[1,3]dioxol-5-ylmethylene-2-methylsulfanyl-thiazol-4-one were dissolved in NMP to which was added a solution of potassium tert.butoxide in hexane (1.1 eq.). The colour changed to orange. To this was added as a solid cyanamide (1.2 eq.). The reaction was heated at 80° C. under Ar. for 3 h HPLC indicated complete transformation. 150 ml EtOAc were added and washed with 0.1N HCl twice. The organic layer was then washed extensively with brine. The solvent was dried and evaporated to dryness leading to a yellowish solid. The crude was purified on Parallel Flex system affording a yellow solid, which was dissolved in TBF followed by 1 equivalent of 1N KOH. 20 ml of water were added and the frozen solution was lyophilised yielding 107 mg (51%) of 5-Benzo[1,3]dioxol-5-ylmethylene-4-oxo-thiazolidin-2-ylidene-cyanamide as potassium salt.

HPLC: 2.97 min. LC-MS: M/Z ESI: 1.30 min, 272.06 (M−1). NMR: $^1$H NMR (D)MSO-d6) (potassium salt). δ 7.36 (s, 1H), 6.98-7.07 (m, 4H), 6.08 (s, 2H).

The following compounds were synthesized according to the preparation of Example 19 using suitable starting materials:

Example 20

Preparation of 5-Benzo[1,3]dioxol-5-ylmethylene-thiazolidine-2,4-dione 2-(O-methyl-oxime)

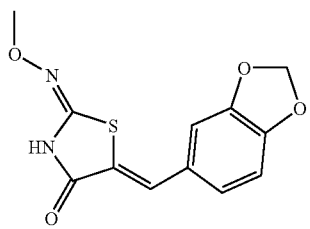

HPLC: 3.34 min. LC-MS: M/Z ESI: 1.61 min, 277.19 (M−1). NMR: $^1$H NMR (D)MSO-d6) (parent compound). δ 12.1 (s, 1H), 7.55 (s, 1H), 7.05-7.14 (m, 3H), 6.12 (s, 2H), 3.80 (s, 3H).

Example 21

Preparation of 4-Oxo-5-quinoxalin-6-ylmethylene-thiazolidin-2-ylidene-cyanamide

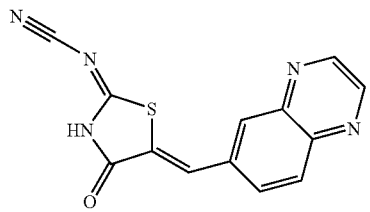

HPLC: 2.51 min. LC-MS: M/Z ESI: 1.07 min, 280.09 (M−1). NMR: $^1$H NMR (DMSO-d6) (parent compound). δ 12.80 (b s, 1H), 9.00 (s, 2H), 8.05-8.32 (m, 4H).

Example 22: 5-Benzo[1,3]dioxol-5-ylmethylene-2-benzylimino-thiazolidin-4-one

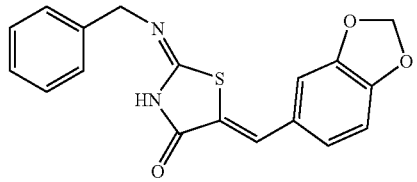

5-Benzo[1,3]dioxol-5-ylmethylene-2-thioxo-thiazolidin-4-one (100 mg, 0.37 mmol) were dissolved in EtOH/water, followed by 60 mg of Na$_2$CO$_3$. The reaction was stirred for 30 min and benzylamine (122 μl, 3 eq.) was added. The reaction mixture was refluxed for 2 h. and the solvents were evaporated. The crude was purified by Parallel Flex chromatography.

Yield: 31 mg (23%). HPLC: 3.66 min. LC-MS: MWZ ESI: 1.58 min, 339.13 (M+1). $^1$H NMR (DMSO-d6) a 10.0 (s, 1H), 7.54 (s, 1H), 7.07-7.37 (m, 8H), 6.10 (s, 2H), 4.72 (s, 2H).

The following compounds were prepared according to the synthesis of Example 24 using suitable starting materials:

Example 23

Preparation of 2-Benzylimino-5-quinolin-6-ylmethylene-thiazolidin-4-one

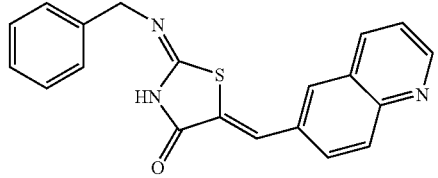

Example 24

Preparation of 2-Propylimino-5-quinolin-6-ylmethyl-ene-thiazolidin-4-one

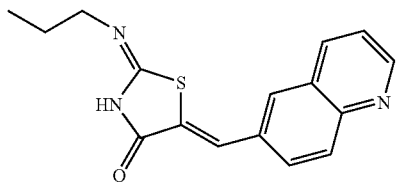

Yield: 100 mg (80%). HPLC: 2.45 min. LC-MS: M/Z ESI: 1.32 min. 298.03 (M+1).

Example 25

5-Benzo[1,3]dioxol-5-ylmethylene-2-propylimino-thiazolidinone

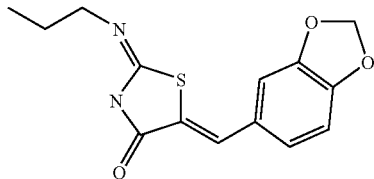

Yield: 22 mg (14%). HPLC: 2.11 min. LC-MS: M/Z ESI: 1.46 min, 291.03 (M+1).

Example 26

Preparation of 5-(4-Dimethylamino-quinazolin-6-ylmethylene)-2-methylimino-thiazolidin-4-one

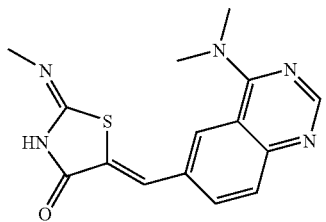

Yield: 42 mg (22%). HPLC: 1.48 min. LC-MS: M/Z ESI: 1.17 min, 314.05 (M+1).

The HPLC, NMR and MS data provided in the examples described below were obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The purifications were obtained as followed: Parallel Flex Biotage, Preparative HPLC Waters Prep LC 4000 System equipped with columns Prep Nova-Pak®HR C186 μm 60 Å, 40×30 mm (up to 100 mg) or 40×300 mm (up to 1 g). All the purifications were performed with a gradient of MeCN/H$_2$O 0.09% TFA.

Example 27

Preparation of a Pharmaceutical Formulation

The following formulation examples illustrate representative pharmaceutical compositions according to the present invention being not restricted thereto.

Formulation 1—Tablets

A compound of formula (I) is admixed as a dry powder with a dry gelatin binder in an approximate 1:2 weight ration. A minor amount of magnesium stearate is added as a lubricant The mixture is formed into 240-270 mg tablets (80-90 mg) of active 2-imino-azolinone compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active 2-imino-azolinone compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavour, and colour are diluted with water and added with stirring. Sufficient water is then added to produce a total volume of 5 mL.

Formulation 4—Tablets

A compound of Formula (I) is admixed as a dry powder with a dry gelatin binder in an approximate 1:2 weight ratio. A minor amount of magnesium steerate is added as a lubricant The mixture is formed into 450-900 mg tablets (150-300 mg of active 2-imino-azolinone compound) in a tablet press.

Formulation 5—Injection

A compound of Formula (I) is dissolved in a buffered sterile saline injectable aqueous medium to a concentration of approximately 5 mg/ml.

Example 28

Biological Assays

The compounds of the present invention may be subjected to the following assays:

a) High Throughput PI3K Lipid Kinase Assay (Binding Assay):

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 μl of the test compound of Formula (D) (solubilized in 6% DMSO; to yield a concentration of 100, 30, 10, 3, 1, 0.3, 0.1, 0.03, 0.01, 0.001 μM of the test compound), the following assay components are added. 1) 5 μl (58 ng) of Human recombinant GST-PI3Kγ (in Hepes 40 mM, pH 7.4, DTT 1 mM and ethylenglycol 5%) 2) 10 μl of lipid micelles and 3) 10 μl of Kinase buffer ([$^{33}$P]γ-ATP 45 μM/60 nCi, MgCl$_2$ 30 mM, DTT 1 mM, β-Glycerophosphate 1 mM, Na$_3$VO$_4$ 100 μM, Na Cholate 0.3%, in Hepes 40 mM, pH 7.4). After incubation at room temperature for 180 minutes, with gentle agitation, the reaction is stopped by addition of 60 μl of a solution containing 100 μg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in respect of PI3Kγ refer to the IC$_{50}$ (μM), i.e. the amount necessary to achieve 50% inhibition of said target. Said values show a considerable potency of the 2-imino-azolinone-vinyl fused-benzene compounds with regard to PI3Kγ.

The tested compounds according to Formula (I) display an inhibition (IC$_{50}$) with regard to PI3Kγ of less than 10 μM, more preferred equal or less than 1 μM.

Examples of inhibitory activities for test compounds 16, 20, 21, 22 & 26 are set out in Table 1.

TABLE 1

IC$_{50}$ values of 2-imino-azolinone-vinyl fused-benzene derivatives against PI3Kγ.

| Example No | PI3Kγ, IC$_{50}$ (μM) |
|---|---|
| 20 | <1.0 |
| 21 | <1.0 |
| 26 | <1.0 |
| 16 | <1.0 |
| 22 | <1.5 | b) Cell Based ELISA to Monitor PI3K Inhibition:

Measurement of Akt/PKB phosphorylation in macrophages after stimulation with human recombinant Complement 5a (C5a) from Sigma (C5788): Raw 264: Raw 264-7 macrophages (cultured in DMEM-F12 medium containing 10% Fetal Calf serum and antibiotics) are plated at 20,000 cells/well in a 96 MTP 24 h before cell stimulation. Previous to the stimulation with 50 nM of Complement 5a during 5 minutes, Cells are serum starved for 2 h, and pre-treated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% H$_2$O$_2$ and 0.1% Sodium Azide in PBS/Triton and washed 3 times in PBS/Triton. Cells are then blocked by 60 minutes incubation with 10% foetal calf serum in PBS/Triton. Next, phosphorylated AKWPKB is detected by an overnight incubation at 4° C. with first antibody (anti phospho Serine 473 Akt IHC, Cell Signalling) diluted 800-fold in PBS/Triton, containing 5% bovine serum albumin (BSA). After 3 washes in PBS/Triton, cells are incubated for 60 minutes with a peroxidase conjugated goat-anti-rabbit antibody (1/400 dilution in PBS/Triton, containing 5% BSA), washed 3 times in PBS/Triton, and 2 times in PBS and further incubated in 100 μl of substrate reagent solution (R&D) for 20 minutes. The reaction is stopped by addition of 50 μl of 1 M SO$_4$H$_2$ and absorbance is read at 450 nm.

The values indicated reflect the percentage of inhibition of AKT phosphorylation as compared to basal level. Said values show a clear effect of the 2-imino-azolinone-vinyl fused-benzene compounds on the activation of AKT phosphorylation in macrophages.

For example the compound of Example 8, when used at 10 μM, completely inhibits (100% inhibition) C5a-mediated AKT phosophorylation. The compound of Example 10, when used at 10 μM, inhibits 80% of the C5a-mediated AKT-phosphorylation.

REFERENCE LIST

1. Vanhaesebroeck et al., *Trends Biochem. Sci.* 22(7) p. 267-72 (1997);
2. Leslie et al., *Chem. Rev.* 101(8) p. 2365-80 (2001);
3. Katso et al., *Annu. Rev. Cell. Dev. Biol.* 17 p. 615-75 (2001);
4. Toker et al., *Cell. Mol. Life Sci.* 59(5) p. 761-79 (2002);
5. Vanhaesebroeck, *Exp. Cell. Res.* 25(1) p. 239-54 (1999)
6. Stein, *Mol. Med. Today* 6(9) p. 347-57 (2000);
7. Wyman et al., *Immunol Today* 21(6) p. 260-4 (2000);
8. Hirsch et al., *Science* 287 (5455) p. 1049-53 (2000);
9. Hirsch et al., *FASEB J.* 15(11) p. 2019-21 (2001);
10. Gerard et al., *Nat Immunol.* 2(2) p. 108-15 (2001);
11. Panayotou et al., *Trends Cell Biol.* 2 p. 358-60 (1992);
12. Parker et al., *Current Biology*, 5 p. 577-99 (1995);
13. Yao et al., *Science,* 267 p. 2003-05 (1995);
14. Pages et al., *Nature,* 369 p,327-29 (1994);
15. Rudd, *Immunity* 4 p. 527-34 (1996);
16. Fraser et al., *Science,* 251 p. 313-16 (1991);
17. Lopez-Ilasaca et al., *J. Biol. Chem.* 273(5) p. 2505-8 (1998);
18. Lawlor et al., *J. Cell. Sci.* 114(Pt 16) p. 2903-10 (2001);
19. Laffargue et al., *Immunity* 16(3) p. 441-51 (2002);
20. Stephens et al., *Curr. Opinion Cell Biol.* 14(2) p. 203-13 (2002);
21. Fruman et al., *Annu. Rev. Biochem.,* 67 p. 481-507 (1998);
22. Thelen et al., *Proc. Natl. Acad. Sci. USA,* 91 p. 4960-64 (1994);
23. Janusz et al., *J. Med. Chem.,* 41, 18, 3515-3529 (1998);
24. Roué et al., *Tetrahedron,* 55, 14729-14738 (1999);
25. EP0697410;
26. Brummond et al., *J.O.C.,* 64, 1723-1726 (1999).

The invention claimed is:

1. An imino-azolinone-vinyl fused-benzene compound or its salt according to Formula (I),

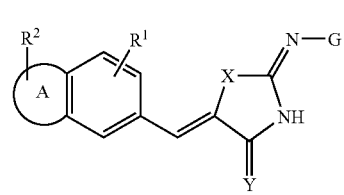

wherein A is an 5-8 membered heterocyclic group or an carbocyclic group which may be fused with an aryl, an heteroaryl, an cycloalkyl or an heterocycloalkyl;

X is S, O or —NR$^3$;

Y is S or O;

R$^1$ is selected from the group consisting of H, CN, carboxy, acyl, C$_1$-C$_6$-alkoxy, halogen, hydroxy, acyloxy, C$_1$-C$_6$-alkyl carboxy, C$_1$-C$_6$-alkyl acyloxy, C$_1$-C$_6$-alkyl alkoxy, alkoxycarbonyl, C$_1$-C$_6$-alkyl alkoxycarbonyl, aminocarbonyl, C$_1$-C$_6$-alkyl aminocarbonyl, acylamino, C$_1$-C$_6$-alkyl acylamino, ureido, C$_1$-C$_6$-alkyl ureido, amino, C$_1$-C$_6$-alkyl amino, ammonium, sulfonyloxy, C$_1$-C$_6$-alkyl sulfonyloxy, sulfonyl, C$_1$-C$_6$-alkyl sulfonyl, sulfinyl, $C_1$-$C_6$-alkyl sulfinyl, sulfanyl,$C_1$-$C_6$-alkyl sulfanyl, sulfonylamino, $C_1$-$C_6$-alkyl sulfonylamino and carbamate;

$R^2$ is selected from the group consisting of H, halogen, acyl, amino, $C_1$-$C_6$-alkyl, $C_2$-$C_6$-alkenyl, $C_2$-$C_6$-alkynyl, $C_1$-$C_6$-alkyl carboxy, $C_1$-$C_6$-alkyl acyl, $C_1$-$C_6$-alkyl alkoxycarbonyl, $C_1$-$C_6$-alkyl aminocarbonyl, $C_1$-$C_6$-alkyl acyloxy, $C_1$-$C_6$-alkyl acylamino, $C_1$-$C_6$-alkyl ureido, $C_1$-$C_6$-alkyl carbamate, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, heteroaryl, $C_3$-$C_8$-cycloalkyl or heterocycloalkyl, $C_1$-$C_6$-alkyl aryl, $C_1$-$C_6$-alkyl heteroaryl, $C_2$-$C_6$-alkenyl-aryl or -heteroaryl, $C_2$-$C_6$-alkynyl aryl or -heteroaryl, carboxy, cyano, hydroxy, $C_1$-$C_6$-alkoxy, nitro, acylamino, ureido, sulfonylamino, sulfanyl, and sulfonyl;

G is phenyl sulfonyl, 4-methylphenyl sulfonyl, methyl sulfonyl, ethyl sulfonyl, 6-chloropyridine-3-sulfonyl, thiophene-2-carboxylic acid methyl ester-3-sulfonyl, 5-chloro-1,3-dimethyl-1H-pyrazole-4 sulfonyl, 3-chlorophenyl sulfonyl, 2-chlorophenyl sulfonyl, quinoline-8-sulfonyl, biphenyl-2-sulfonyl, or pyridine-3-sulfonyl;

$R^3$ is selected from the group consisting of H and $C_1$-$C_6$-alkyl; with the proviso that the following compounds are excluded :

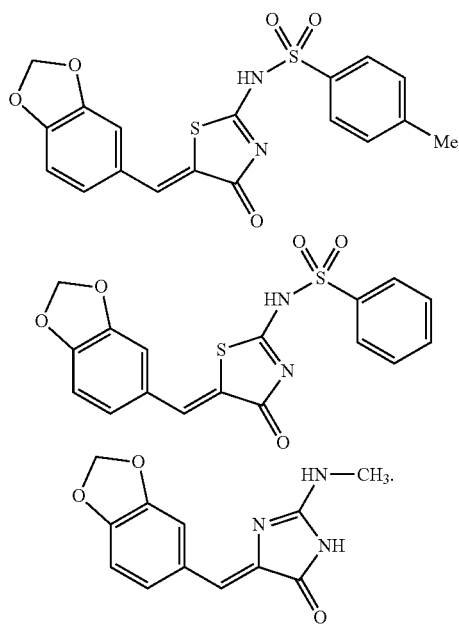

2. The imino-azolinone-vinyl fused-benzene compound or its salt according to claim 1, wherein A is selected from the group consisting of 2H-(benzo-1,3-dioxolanyl), 2H, 3H-benzo-1,4-dioxanyl, 2,3dihydrobenzofuranyl, anthraquinonyl, 2,2-difluorobenzo-1,3-dioxolenyl, 1,3dihydrobenzofuranyl, benzofuranyl, 4-methyl-2H-benzo-1,4-oxazin-3-onyl, pyridinyl, pyrazinyl, and 4-methyl-2H, 3H-benzo-1,4-oxazinyl.

3. The imino-azolinone-vinyl fused-benzene compound or its salt according to claim 2, wherein A is a dioxolenyl or a pyridinyl moiety.

4. The imino-azolinone-vinyl fused-benzene compound or its salt according to claim 1, wherein $R^1$, $R^2$, or $R^1$and $R^2$ are H.

5. The imino-azolinone-vinyl fused-benzene compound or its salt according to claim 1, wherein X is S, Y is O, $R^1$and $R^2$ are H, and A is a dioxolenyl or pyridinyl moiety.

6. The imino-azolinone-vinyl fused-benzene compound or its salt according to claim 1, selected from the group consisting of :

N-(5-Benzo[1,3]dioxol-5-ylmethylene-4-oxo-thiazolidin-2ylidene)-2-chloro-benzene sulfonamide;

Ethanesulfonic acid (5-benzo[1,3]dioxol-5-ylmethylene-4-oxo -thiazolidin-2-ylidene) -amide;

N-(5-Benzo[1,3]dioxol-5-ylmethylene-4-oxo-thiazolidin-2-ylidene)-3-chloro-benzene sulfonamide;

5-Chloro-1,3-dimethyl-1H-pyrazole-4-sulfonic acid (5-benzo[1,3]dioxol-5-yl methylene -4-oxo-thiazolidin-2-ylidene)-amide;

3-(5-Benzo[1,3]dioxol-5-ylmethylene-4-oxo-thiazolidin-2-ylidenesulfamoyl) -thiophene-2-carboxylic acid methyl ester;

6-Chloro-pyridine-3-sulfonic acid (5-benzo[1,3 ]dioxol-5-ylmethylene-4-oxo -thiazolidin-2-ylidene)-amide;

Quinoline-8-sulfonic acid (5-benzo[1,3]dioxol-5-ylmethylene-4-oxo-thiazolidin-2-ylidene)-amide;

N-(5-Benzo[1,3]dioxol-5-ylmethylene-4-oxo-thiazolidin-2-ylidene)-methane sulfonamide;

N-[5-(2,2-Difluoro-benzo[1,3]dioxol-5-ylmethylene)-4-oxo -thiazolidin-2-ylidene]-benzenesulfonamide;

N-[5-(2,2-Difluoro-benzo[1,3]dioxol-5-ylmethylene)-4-oxo -thiazolidin-2-ylidene]-4-methyl-benzenesulfonamide;

N-[5-(2,2-Difluoro-benzo[1,3]dioxol-5-ylmethylene)-4-oxo -thiazolidin-2-ylidene]-methanesulfonamide;

Biphenyl-2-sulfonic acid (5-benzo[1,3]dioxol-5-ylmethylene-4-oxo-thiazolidin-2-ylidene)-amide;

Pyridine-3-sulfonic acid (5-benzo[1,3]dioxol-5-ylmethylene-4-oxo-thiazolidin-2-ylidene)-amide;

3-(4-Oxo-5-quinolin-6-ylmethylene-thiazolidin-2-ylidenesulfamoyl)-thiophene-2-carboxylic acid methyl ester; and 2-Chloro-N-(4-oxo-5-quinolin-6-ylmethylene-thiazolidin-2-ylidene)-benzene Sulfonamide.

7. A composition comprising a carrier, adjuvant, diluent, excipient, or a combination thereof and an imino-azolinone-vinyl fused-benzene compound or its salt according to Formula (I)

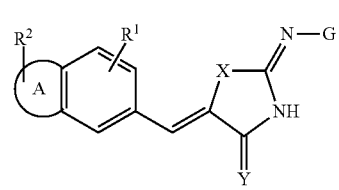

wherein A is an 5-8 membered heterocyclic group or an carbocyclic group which may be fused with an aryl, an heteroaryl, an cycloalkyl or an heterocycloalkyl;

X is S, O or —$NR^3$;

Y is S or O;

$R^1$ is selected from the group consisting of H, CN, carboxy, acyl, $C_1$-$C_6$-alkoxy, halogen, hydroxy, acyloxy, $C_1$-$C_6$-alkyl carboxy, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, acylamino, $C_1$-$C_6$-alkyl acylamino, ureido, $C_1$-$C_6$-alkyl ureido, amino, C,-$C_6$-alkyl amino, ammonium, sulfonyloxy, $C_1$-$C_6$-alkyl sulfonyloxy, sulfonyl, $C_1$-$C_6$-alkyl sulfonyl, sulfinyl, $C_1$-$C_6$-alkyl sulfinyl, sulfanyl, $C_1$-$C_6$-alkyl sulfanyl, sulfonylamino, $C_1$-$C_6$-alkyl sulfonylamino and carbamate;

$R^2$ is selected from the group consisting of H, halogen, acyl, amino, $C_1$-$C_6$-alkyl, $C_2$-$C_6$-alkenyl, $C_2$-$C_6$-alkynyl, $C_1$-$C_6$-alkyl carboxy, $C_1$-$C_6$-alkyl acyl, $C_1$-$C_6$-alkyl alkoxycarbonyl, $C_1$-$C_6$-alkyl aminocarbonyl, $C_1$-$C_6$-alkyl acyloxy, $C_1$-$C_6$-alkyl acylamino, $C_1$-$C_6$-alkyl ureido, $C_1$-$C_6$-alkyl carbamate, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, heteroaryl, $C_3$-$C_8$-cycloalkyl, $C_3$-$C_8$-heterocycloalkyl, $C_1$-$C_6$-alkyl aryl, $C_1$-$C_6$-alkyl heteroaryl, $C_2$-$C_6$-alkenyl-aryl, $C_2$-$C_6$-alkenyl-heteroaryl, $C_2$-$C_6$-alkynyl aryl, $C_2$-$C_6$-alkynyl-heteroaryl, carboxy, cyano, hydroxy, $C_1$-$C_6$-alkoxy, nitro, acylamino, ureido, sulfonylamino, sulfanyl, and sulfonyl;

G is phenyl sulfonyl, 4-methphenyl sulfonyl, methyl sulfonyl, ethyl sulfonyl, 6-chloropyridine-3-sulfonyl, thiophene-2-carboxylic acid methyl ester-3-sulfonyl, 5-chloro-1,3-dimethyl-1H-pyrazole-4 sulfonyl, 3-chlorophenyl sulfonyl, 2-chlorophenyl sulfonyl, quinoline-8-sulfonyl, biphenyl-2-sulfonyl, or pyridine-3-sulfonyl; $R^3$ is selected from the group consisting of H and $C_1$-$C_6$-alkyl

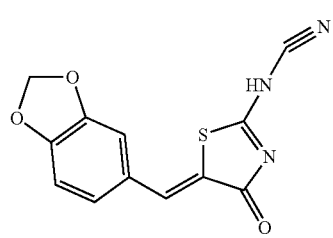

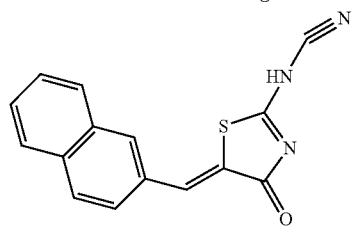

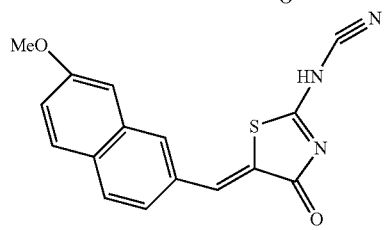

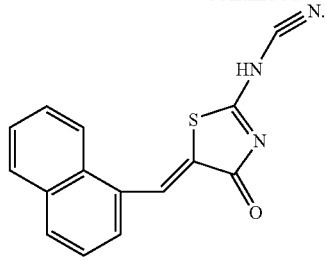

8. A pharmaceutical composition comprising at least one thiazolidinone-vinyl fused-benzene compound or its salt according to claim 1 and a pharmaceutically acceptable carrier, diluent, excipient, or combination thereof.

9. A method of preparing a 2-imino-azolinone-vinyl fused-benzene compound or its salt of Formula (I) according to claim 1 comprising derivatizing the imine of Formula Ia with the group G to form the vinyl fused-benzene derivative or its salt

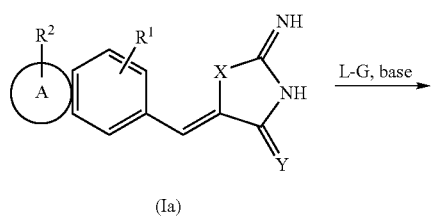

(Ia)

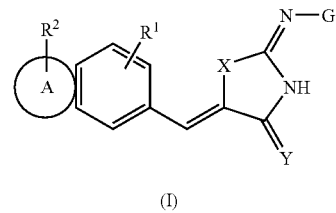

(I)

wherein L is a leaving group.

* * * * *